US011679384B2

(12) United States Patent
Smith

(10) Patent No.: US 11,679,384 B2
(45) Date of Patent: Jun. 20, 2023

(54) BIOASSAY CARRIER AND PREPARATION THEREOF

(71) Applicant: GERMITEC, Ivry-sur-Seine (FR)

(72) Inventor: Adrian Edward Smith, Emerald Hills, CA (US)

(73) Assignee: GERMITEC, Ivry-sur-Seine (FR)

( * ) Notice: Subject to any disclaimer, the term of this patent is extended or adjusted under 35 U.S.C. 154(b) by 616 days.

(21) Appl. No.: 16/631,704

(22) PCT Filed: Jul. 21, 2017

(86) PCT No.: PCT/US2017/043264
§ 371 (c)(1),
(2) Date: Jan. 16, 2020

(87) PCT Pub. No.: WO2019/017964
PCT Pub. Date: Jan. 24, 2019

(65) Prior Publication Data
US 2020/0164358 A1    May 28, 2020

(51) Int. Cl.
*B01L 3/02* (2006.01)
*A61L 2/28* (2006.01)
(Continued)

(52) U.S. Cl.
CPC .............. *B01L 3/0268* (2013.01); *A61L 2/28* (2013.01); *B01J 19/0046* (2013.01); *B01L 9/52* (2013.01);
(Continued)

(58) Field of Classification Search
CPC .. B01L 3/0268; B01L 9/52; B01L 2300/0822; B01L 2300/089;
(Continued)

(56) References Cited

U.S. PATENT DOCUMENTS

| 5,743,960 A | 4/1998 | Tisone |
| 6,110,426 A | 8/2000 | Shalon et al. |

(Continued)

FOREIGN PATENT DOCUMENTS

| CN | 106916738 | 7/2017 | |
| EP | 2 344 679 | * 7/2011 | ....... A61B 5/150022 |

OTHER PUBLICATIONS

Hui, Liu, "Experimental Techniques for Modern Food Microbiology", Feb. 2017, p. 137, China Light Industry Press.
(Continued)

*Primary Examiner* — Jennifer Wecker
*Assistant Examiner* — Jonathan Bortoli
(74) *Attorney, Agent, or Firm* — B. Aaron Schulman, Esq.; Stites & Harbison, PLLC

(57) ABSTRACT

Embodiments are directed towards methods and systems of depositing a uniform test-pathogen mixture onto a test article for testing the sterilization efficacy of an electromagnetic radiation or other sterilization process. The system includes a holding mechanism configured to removably secure the test article to the system. The system also includes a test-pathogen dispenser configured to uniformly deposit the test-pathogen mixture onto a reference surface of the test article. The system is structured so that at least one of the test article and the test-pathogen dispenser moves relative to the other. A plurality of test-pathogen mixture droplets or lines is deposited onto the reference surface in a predetermined test-pathogen pattern, such as, for example, a plurality of rows and columns of droplets. A distance from a dispenser tip of the test-pathogen dispenser to the reference surface of the test article may be determined to help maintain consistency between test-pathogen mixture droplets or lines.

22 Claims, 13 Drawing Sheets

(51) Int. Cl.
*B01J 19/00* (2006.01)
*B01L 9/00* (2006.01)

(52) U.S. Cl.
CPC .............. *B01J 2219/00378* (2013.01); *B01J 2219/00527* (2013.01); *B01J 2219/00689* (2013.01); *B01L 2300/0822* (2013.01)

(58) Field of Classification Search
CPC ... B01L 2300/161; A61L 2/28; B01J 19/0046; B01J 2219/00378; B01J 2219/00527; B01J 2219/00689
See application file for complete search history.

(56) References Cited

U.S. PATENT DOCUMENTS

| | | |
|---|---|---|
| 8,530,184 B2 | 9/2013 | Franciskovich et al. |
| 8,691,562 B2 | 4/2014 | Franciskovich et al. |
| 9,012,173 B2 | 4/2015 | Franciskovich et al. |
| 2004/0014029 A1* | 1/2004 | Mutz ................ B01L 3/0293 506/40 |
| 2004/0237822 A1 | 12/2004 | Boland et al. |
| 2007/0000442 A1* | 1/2007 | Schucker ............. B25J 19/023 118/713 |
| 2012/0021406 A1 | 1/2012 | Franciskovich et al. |
| 2013/0217001 A1 | 8/2013 | Franciskovich et al. |
| 2014/0162307 A1 | 6/2014 | Franciskovich et al. |
| 2015/0300929 A1* | 10/2015 | Kirk ...................... G01N 1/312 435/40.51 |
| 2017/0131318 A1 | 5/2017 | Austin et al. |

OTHER PUBLICATIONS

International Search Report for Aplication No. PCT/US2017/043264 dated Mar. 29, 2018.
Written Opinion for International Aplication No. PCT/US2017/043264 dated Mar. 29, 2018.

* cited by examiner

BIOASSAY CARRIER AND PREPARATION THEREOF

BACKGROUND

Technical Field

The present disclosure generally relates to systems and methods of depositing a pathogen on a test article, and more particularly, but not exclusively, to utilization of an automated system for depositing the pathogen uniformly across a test article in a distributed pattern.

Description of the Related Art

Disinfecting processes, which may also be referred to as sterilizing processes if performed to a high level of pathogen removal and/or deactivation, are used to render medical equipment to a biologically "safe" state. These cleaning procedures are important to the medical community and to patients that rely on re-used medical equipment. To reduce the risk of infection to patients, the re-used equipment must have a low presence of pathogen, or "bioburden." Some medical equipment is manufactured aseptically (i.e., in a sterile environment) or sterilized during the manufacturing process and used only once on a given patient. Because it is discarded, this type of medical equipment does not require disinfection or sterilization after use. Other medical equipment, however, is intended for re-use and is returned to a condition suitable for use with the same or another patient. This re-used medical equipment may be disinfected by soaking in a chemical solution between uses or by some other means.

There are many types of medical equipment that are highly specialized, expensive, and for a variety of reasons not practical to discard. Further, this type of medical equipment may be sensitive to, and potentially damaged or rendered not useful by, disinfecting or sterilization with some common methods such as by soaking in chemical solutions, by exposure to toxic gasses or vapors, or by extreme heat such as in an autoclave or oven. One class of medical devices that may not be compatible with harsh disinfection/sterilization methods are imaging probes, such as optical, ultrasonography, and other internal and external imaging probes.

Exposure to X-rays, gamma rays, and other wavelengths of electromagnetic radiation has been found to be useful in sterilizing some types of medical equipment. However, the efficiency and efficacy of sterilization using electromagnetic radiation can vary depending on the amount and type(s) of pathogen on the medical equipment, the distribution of pathogen on the medical equipment, the surface material of the medical equipment, and the surface contours, structures, and condition of the medical equipment. Further, the type of energy used, which is often defined by wavelength, the power level, which is how much energy is being delivered per unit time, the total energy dosage delivered during the electromagnetic radiation process, and other variables will determine whether the medical equipment has been disinfected or sterilized to the appropriate level.

Disinfectants and systems designed to deliver disinfectants are approved for sale in the United States and other markets subject to testing in accordance with various standards, including the Association of Official Analytical Chemists (AOAC) biological test protocols. These tests require various pathogens (i.e., live bacteria and spores, viruses, molds, fungi, and the like) to be inoculated onto standard carriers. Because historically the disinfectants were liquid chemicals and historically the reused medical devices were typically metallic structures such as scalpels, clamps, retractors, dental tools, and the like, the test methods evolved to reflect liquid chemical disinfection processes and to reasonably emulate these processes with an easy-to-perform and reproducible test method. The standard carriers that evolved and are now in common use are conventionally made of porcelain, glass, stainless steel, or some combination thereof. The standard carriers may be simple discs or rectangular coupons. In addition, or in the alternative, the standard carriers may be arranged in a "standard" form called a "penicylinder," which is a small cylindrical carrier whose use arose from the perceived need for a compact, small reference surface that could be easily inoculated in a moderately sized test tube containing inoculating suspension. Once prepared, these penicylinders are exposed to liquid disinfectants by complete immersion, soaking, and often some agitation, for a range of exposure intervals. Following disinfection, the carriers are subsequently washed to recover remaining viable pathogen and bioassays performed to quantitate the results. Likewise, hand tied "suture loops" of DACRON, silk thread, or another suitable material, also became commonplace for tests directed at evaluating disinfection efficacy of liquid disinfectants used on medical products or devices that are compatible with soaking in liquids.

Typically, to complete the qualification process of a particular disinfection procedure with a particular medical product or device, testing is performed on actual medical devices in so-called "simulated use" tests. To prepare a carrier or medical device for testing, the standard approach employed in a biological test lab is to hand-pipette droplets of a pathogen-laced, water-based suspension onto the test article or, if appropriate, to fully immerse the test article in a suspension of pathogen.

When testing medical devices that are not appropriate for full immersion in liquids or that cannot be exposed to certain toxic chemicals and gasses, the hand pipetting approach is usually the only practical manner available for inoculating the medical device or test carrier. The distribution of pathogen that results, however, is often highly inconsistent and misrepresentative of the actual contamination that would result by contamination in vivo. While a specifically defined test area is supposed to be inoculated, simply placing a small volume of suspension containing a known number (i.e., count, concentration) of pathogen on the target surface does not result in the subsequent distribution of said pathogen across the target surface. Unlike fully immersing a penicylinder or suture loop where the pathogen tends to distribute uniformly across the entire surface, an unrealistically high concentration of pathogen results at the site where the droplet was deposited. The production of a suitable test article should seek to create a biologically relevant and representative population density in "counts" or "colony forming units" (CFUs) per unit area, and the production of test articles should be reproducible, but this does not happen because these hand pipetting approaches are quite variable and dependent on technique.

Producing test articles by hand pipetting has shown steady improvement in results as the size of the droplets is reduced, the number of droplets is increased, and the droplets are distributed over the entire test area defined by the AOAC standard. A practical limit for conducting this process by hand deposits 100 or so droplets of approximately the same volume. Nevertheless, the hand pipetting process still tends to overly concentrate the pathogen in small areas of the test article because a relatively large amount of pathogen is still deposited at one time in one spot. Further, due to surface tension of the suspensions and related non-wetting of many surfaces commonly used, the deposited droplets typically do not "spread out," and instead remain as a spherical or hemispherical drop, which then dries, again leaving an unrealistically high concentration of pathogen "residue" in a very small area.

Hand pipetting large numbers of droplets is also limited by human capabilities. It is difficult for a human to position and dispense the drops accurately, and a human's ability to focus and concentrate so as to perform this task repeatedly across many sample carriers is limited. What is more, humans cannot reasonably be expected to accurately and reproducibly deposit the very small volumes typically dispensed by hand pipettes.

Hand pipetting procedures to produce test articles also have other shortcomings. For example, the hand pipetting methods may also lead to cross contamination, where material may be transferred from one location to another. As another example, some surfaces may be substantially more wetted than others, which leads to some "dot areas" being larger than others, and hence the resulting distribution of pathogen is less homogenous across the entire treated area. Another factor that may lead to unpredictable results derives from commonly used "half-hemisphere" approximations. In these cases, a half-hemisphere assumes that the volume of a spherical droplet is constrained within a half sphere once the liquid is deposited on a surface, and the diameter that results is thereby greater than that of the original full sphere.

In some cases, common physico-chemical methods and techniques are used to improve surface wetting in an attempt to achieve better homogeneity of the resulting pathogen distribution. Such methods may modify the test article surface by corona discharge or pretreatment with a surfactant or other chemical wetting agent. Other methods add a chemical agent to the pathogen suspension, but these methods must be approached with caution because the chemical agent may interfere with the test accuracy, affect the pathogen's susceptibility to the disinfectant, and induce other errors.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which, in and of itself, may also be inventive.

BRIEF SUMMARY

To enhance the reproducibility of the test results, the inventive concepts now disclosed provide a significant improvement over the standard biological lab approach of hand-pipetting a pathogen-laced suspension onto test articles. The hand pipetting test preparation has practical limitations of 100 or so droplets of approximately a microliter ($\mu l$) or half-microliter volume, and even under these conditions the area distribution of pathogen (CFUs/area) in these limited samples are often not accurately or consistently reproducible. It has been recognized that volume resolution and accuracy of hand pipettes are increasingly less accurate as dispensed volumes drop below about 0.5 $\mu l$ per dispensed sample. Although some manufacturers claim resolution to 0.2 $\mu l$ for their smallest total tip volumes, reproducibility has been recognized as mediocre at these "small" volumes (e.g., six percent (6%) relative standard deviation (RSD) is typical). In addition, even a reasonable number of droplets for a human to track and dispense by hand is difficult because human deposition leads to poor placement accuracy and reproducibility between hand-dispensed samples. Hence an automated and more reproducible system is envisioned.

In the present disclosure, embodiments of an automated, acceptably precise, liquid dispensing system for creating test articles treated with biological suspensions is described. The automated system is arranged to produce test articles for performance verification and for validation of medical device disinfection systems. In some embodiments, a micro-drop delivery valve is mounted to an XYZ dispensing robot table that provides significant improvement in reproducibility of artificially contaminated test articles. The test articles produced by the automated system are more representative of the surface of a "dirty" probe, where the pathogen is well distributed and not overly concentrated in certain locations, as is the case when depositing a relatively large amount of pathogen at one time, in one spot, by a hand pipetting method. The envisioned automated system can in essence achieve uniform "coating" of desired areas of test articles by depositing discrete micro-droplets in close proximity to each other. In some embodiments, the micro-droplets are on the order of 50-200 droplets per square centimeter ($cm^2$), and in some embodiments, a desirable target is 100 droplets/1.0 $cm^2$. In other embodiments, a continuous bead, spray, or sheet of pathogen-laced liquid suspension is deposited on the test article.

Embodiments are directed towards methods and systems of depositing a uniform test-pathogen mixture onto a test article for testing the sterilization efficacy of a particular process such as an electromagnetic radiation process on the test article. The system includes a holding mechanism configured to removably secure the test article to the system. The system also includes a test-pathogen dispenser, also referred to as a pathogen distribution mechanism, configured to uniformly deposit the test-pathogen mixture onto a reference surface of the test article. The system is structured so that either the test article or the test-pathogen dispenser, or both, traverse relative to one another to allow for the uniform deposition of the test-pathogen mixture. In various embodiments, a plurality of test-pathogen mixture droplets or lines are deposited onto the reference surface in a predetermined test-pathogen pattern, such as, for example, a plurality of rows and columns of droplets. In various embodiments, a distance from a dispenser tip of the test-pathogen dispenser to the reference surface of the test article is determined using contact sensors (e.g., force-feedback sensors when the dispenser tip touches the test article, a secondary probing element to touch the surface, or the like) or non-contact sensors (e.g., light-based sensors, acoustic-based sensors, detectors based on electromagnetic fields, or the like). This distance is utilized, for example, to maintain consistency between test-pathogen mixture droplets or lines.

In a first embodiment, an apparatus includes a holding mechanism configured to removably secure a test article such that at least one reference surface of the test article is exposed and a pathogen distribution mechanism configured to uniformly distribute a test-pathogen mixture across a reference area of the exposed test article.

In some of these embodiments, the reference area is treated to improve its surface wetting properties, and in some, the reference area is treated to improve adhesion of the test-pathogen mixture. In some embodiments, the test-pathogen mixture includes at least one type of virus, bacteria, fungus, yeast-mold, spore, or chemotherapeutic agent.

In some of these first embodiments, uniform distribution of the test-pathogen mixture includes a substantially homogeneous distribution of the test-pathogen mixture across the reference area. In other embodiments, uniform distribution of the test-pathogen mixture includes distribution of the test-pathogen mixture as a continuous film across a determined length and a determined width of the reference area. In still other embodiments, uniform distribution of the test-pathogen mixture includes distribution of the test-pathogen mixture as a deposition of one or more continuous lines, each of the one or more continuous lines having a determined length and a determined width. Uniform distribution of the test-pathogen mixture may include distribution of the test-pathogen mixture as a deposition of a plurality of individual droplets in some embodiments, and in others, uniform distribution of the test-pathogen mixture includes distribution of the test-pathogen mixture in a plurality of layers. Sometimes, distribution of the test-pathogen mixture includes a determined time-to-dry between applications of a plurality of portions of the test-pathogen mixture.

In some of the first embodiments, uniform distribution of the test-pathogen mixture includes distribution of the test-pathogen mixture in a determined pattern. The determined pattern may include a plurality of rows and a plurality of columns of droplets the test-pathogen mixture, or the determined pattern may include distribution of the test-pathogen mixture in a plurality of non-touching arrays. In some of these cases, distribution of the test-pathogen mixture in the plurality of non-touching arrays includes a first array deposited and allowed to dry before a second array is deposited. Drying time between deposition of a first droplet in an array and deposition of a second droplet in an array may in some cases be at least 100 milliseconds. Selected ones of the plurality of rows may be offset from adjacent rows, and selected ones of the plurality of columns may be offset from adjacent columns.

An apparatus according to some first embodiments includes an automated positioning system to repeatably move a dispensing mechanism to a plurality of determined locations in proximity to the reference area and an automated dispensing system to direct the dispensing mechanism to repeatably introduce portions of the test-pathogen mixture about a surface of the reference area. In some of these cases, the automated positioning system controls movement of the dispensing mechanism in at least two dimensions, and in these and other cases, the automated positioning system controls movement of the dispensing mechanism in at least three dimensions. In some cases, the automated positioning system is configured to repeatably position at least one orifice of the dispensing mechanism at a pre-determined distance from the reference area. Here, the automated positioning system may include at least one distance sensor to determine a distance between the dispensing mechanism and the surface of the reference area. Also here, the at least one range sensor of the automated positioning system may in some cases be used to confirm distribution of at least some of the test pathogen. In addition or in the alternative, the at least one range sensor of the automated positioning system may include at least one force-feedback sensor. In some embodiments, the automated positioning system includes a control system to generate at least one data structure representing a plurality of contours of the reference area of the exposed test article.

Also in some first embodiments, the dispensing mechanism is arranged to form a defined volume of the test-pathogen mixture as a droplet at an opening of a dispensing orifice and the automated positioning system is arranged to permit the droplet to contact the surface of the reference area. In these cases, the dispensing mechanism may include a dispenser tip, and the dispenser tip may be arranged to induce separation of the droplet when the droplet contacts the surface of the reference area. The dispenser tip may have a substantially cylindrical shape or a substantially cannular shape. The dispenser tip may be one of a plurality of dispenser tips. In these cases, the plurality of dispenser tips may be formed as an array of dispenser tips.

In some first embodiments, the dispensing mechanism includes a separation mechanism to induce separation of the droplet from the dispensing mechanism. In some of these cases, the separation mechanism includes at least one of a vibration device (e.g., an acoustic vibration device, a mechanical vibration device, or another vibration device), an electrostatic charge generation device, a pump, a heater, and an aerator. The dispensing mechanism may be arranged to reciprocate with respect to the reference area. In addition, or in the alternative, the dispensing mechanism may be arranged to rotate with respect to the reference area.

In some cases of the first embodiment, the dispensing mechanism includes a micro-droplet dispenser configured to introduce a substantially accurate volume of the test-pathogen mixture about the surface of the reference area. Here, the micro-droplet dispenser may in some cases be configured to release the substantially accurate volume of the test-pathogen mixture based on a control signal provided by the automated dispensing system. In some embodiments, the dispensing mechanism includes a pressure control device. The pressure control device may be arranged to supply positive pressure and negative pressure, wherein the positive pressure and negative pressure are arranged to form and hold the substantially accurate volume of the test pathogen at an orifice of the dispensing mechanism. In some cases, the droplet has a volume of between about between 0.001 µl and about 0.1 ml.

In a second embodiment, a method of manufacturing a test article for disinfection device testing includes removably securing a test article with a holding mechanism such that at least one reference surface of the test article is exposed, and uniformly distributing a test-pathogen mixture across a reference area of the exposed test article with a pathogen distribution mechanism. In some of these cases, uniform distribution of the test-pathogen mixture includes a substantially homogeneous distribution of the test-pathogen mixture across the reference area and the test-pathogen mixture includes at least one type of virus, bacteria, fungus, yeast-mold, spore, or chemotherapeutic agent. In some cases, uniform distribution of the test-pathogen mixture includes distribution of the test-pathogen mixture in a determined pattern. Uniformly distributing the test-pathogen mixture across the reference area of the exposed test article in some of the second embodiments includes repeatably moving a dispensing mechanism to a plurality of determined locations in proximity to the reference area via an automated positioning system and directing the dispensing mechanism to repeatably introduce portions of the test-pathogen mixture to a surface of the reference area with an automated dispensing system. In these or some other embodiments, directing the dispensing mechanism to repeatably introduce portions of the test-pathogen mixture includes forming a defined volume of the test-pathogen mixture as a droplet at an opening of a dispensing orifice of the dispensing mechanism and permitting the droplet to contact the surface of the reference area.

In a third embodiment a test article production device includes a base and a holding mechanism coupled to the base. The holding mechanism is configured to support a test article. The test article production device includes a gantry structure fixed relative to the base and a test-pathogen dispenser movably secured relative to the gantry structure. The test article production device also includes at least one dispenser tip in fluid communication with the test-pathogen dispenser. Here, the at least one dispenser tip is arranged to deliver portions of test-pathogen from the test-pathogen dispenser to the test article via the at least one dispenser tip, and each portion of test pathogen has a determined volume. In some cases of the third embodiment, the test article production device includes a controller arranged direct movement of one of the test article and the at least one dispenser tip relative to each other. In these cases, the controller is further arranged to direct formation of each portion of test-pathogen. In some of these cases, the controller is arranged to deliver the portions of test-pathogen to the test article in a determined pattern. In some cases of the third embodiment, the test-pathogen dispenser is arranged to store a test-pathogen mixture constituted with least one type of virus, bacteria, fungus, yeast-mold, spore, or chemotherapeutic agent.

This Brief Summary has been provided to introduce certain concepts in a simplified form that are further described in detail below in the Detailed Description. Except where otherwise expressly stated, the Brief Summary does not identify key or essential features of the claimed subject matter, nor is it intended to limit the scope of the claimed subject matter.

BRIEF DESCRIPTION OF THE SEVERAL VIEWS OF THE DRAWINGS

Non-limiting and non-exhaustive embodiments are described with reference to the following drawings. In the drawings, like reference numerals refer to like parts throughout the various figures unless otherwise specified. The sizes and relative positions of elements in the drawings are not necessarily drawn to scale. For example, the shapes of various elements are selected, enlarged, and positioned to improve drawing legibility. The particular shapes of the elements as drawn have been selected for ease of recognition in the drawings.

For a better understanding of the present invention, reference will be made to the following Detailed Description, which is to be read in association with the accompanying drawings in which.

DETAILED DESCRIPTION

Figure 1A:
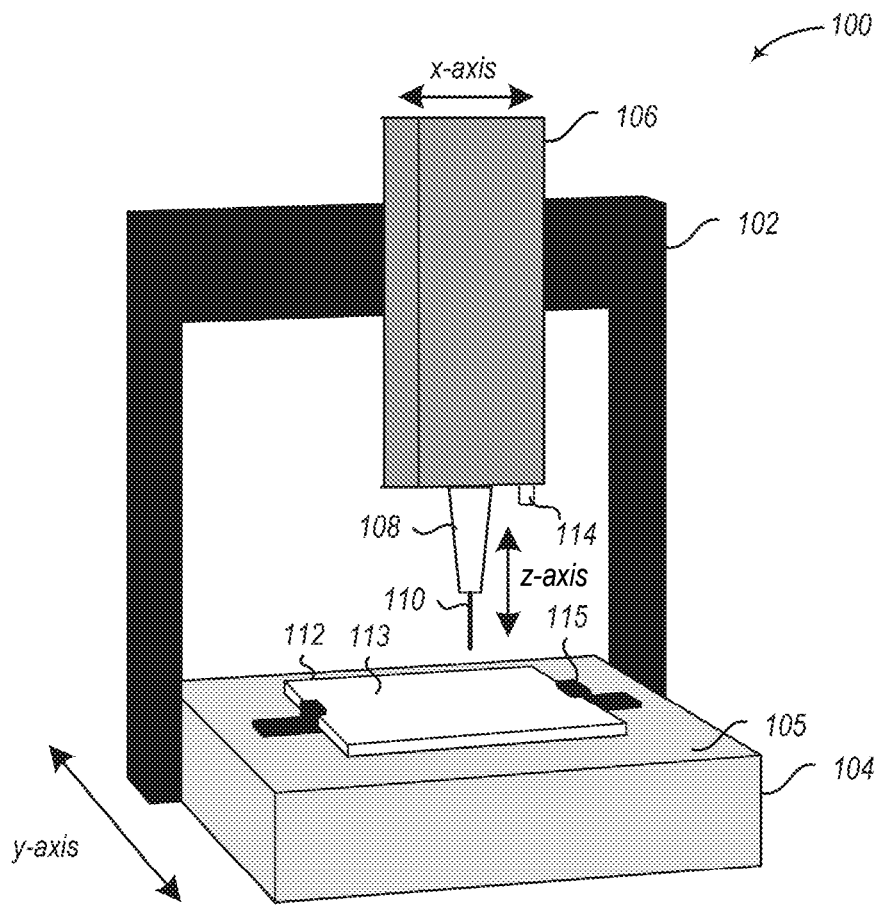
FIGS. 1A-1D show various views of an illustrative example of an automated test-pathogen deposition system.

The following description, along with the accompanying drawings, sets forth certain specific details in order to provide a thorough understanding of various disclosed embodiments. However, one skilled in the relevant art will recognize that the disclosed embodiments may be practiced in various combinations, without one or more of these specific details, or with other methods, components, devices, materials, etc. In other instances, well-known structures or components that are associated with the environment of the present disclosure, including but not limited to the communication systems and networks, have not been shown or described in order to avoid unnecessarily obscuring descriptions of the embodiments. Additionally, the various embodiments may be methods, systems, media, devices, or some other single or combination of such mechanisms. Accordingly, the various embodiments may be entirely hardware embodiments, entirely software embodiments, or embodiments combining software and hardware aspects.

Throughout the specification, claims, and drawings, the following terms take the meaning explicitly associated herein, unless the context clearly dictates otherwise. The term "herein" refers to the specification, claims, and drawings associated with the current application. The phrases "in one embodiment," "in another embodiment," "in various embodiments," "in some embodiments," "in other embodiments," and other variations thereof refer to one or more features, structures, functions, limitations, or characteristics of the present disclosure, and are not limited to the same or different embodiments unless the context clearly dictates otherwise. As used herein, the term "or" is an inclusive "or" operator, and is equivalent to the phrases "A or B, or both" or "A or B or C, or any combination thereof," and lists with additional elements are similarly treated. The term "based on" is not exclusive and allows for being based on additional features, functions, aspects, or limitations not described, unless the context clearly dictates otherwise. In addition, throughout the specification, the meaning of "a," "an," and "the" include singular and plural references.

In the present disclosure, scientific notation is used to represent some numerical values. To dispel confusion in the present disclosure, the alphabetic character "e," when followed by an exponent, is used to represent "times ten raised to the power of." For example, the value 1,000,000 may be represented as 1e6, 1.0e6, or $1\times10^6$. Along these lines, the value 80,450 may be represented as 8.045e4, and the value 0.000008045 may be represented as 8.045e-6. Along these lines, logarithmic terminology may also be used, and in these cases, each logarithm as used herein is applied with a fixed base of ten (10). A logarithm is an inverse operation to exponentiation. Accordingly, the logarithm, or "LOG" as the term may be used herein, of a given number is the exponent to which the fixed base number 10 must be raised to produce the given number. For example, the number "10" raised to the power of "7" (i.e., $10^7$) may also be referred to as 7 LOG.

Disinfection processes lower the presence of one or more viable pathogens in a target area down to or below an acceptably minimum allowable load, wherein a "viable" pathogen is one considered able to reproduce. In contrast, an unviable pathogen is one that is physically removed, killed, destroyed, rendered unable to reproduce, or rendered into a state that is considered safe in some other way. Sterilization processes lower the presence of one or more pathogens in a target area to a point where no colony forming units (CFU) of the given pathogen are detectable, so it is accepted that none of the pathogen is present. Sterilization may thus be described as the limiting condition of continually greater disinfection, which is to the point where no viable pathogen remains. For example, it may be the case that all residual biological matter may need to be removed so that no pyrogen (i.e., cell walls) or other potentially bioactive substance remains, which could cause an immune response in a patient. Disinfecting processes, which may also be referred to as sterilizing processes if performed to a high level of pathogen removal and/or deactivation, are used to render medical equipment to a biologically "safe" state. The terms, disinfect and sterilize, in all of their syntactic contexts, may be used interchangeably herein where such use is not inconsistent with the inventive teachings of the present disclosure.

The term "test article" refers to the item that includes at least one reference surface on which to test the sterilization efficacy of electromagnetic radiation or one or more other sterilization processes. The test article, or at least a reference surface of the test article, can be made of one or more different types of materials, such as, but not limited to steel, ceramic, glass, petroleum-based materials, plant-based materials, mammalian tissue, thread or woven material, or other materials. The test article may be substantially planar (e.g., flat) and generally two-dimensional, and in some embodiments, the reference area is about eight square centimeters (8 cm$^2$). The test article may be three-dimensional having corners, curves, contours, valleys, protuberances, patterns, convex surfaces, concave surfaces, or the like. One non-limiting, non-exhaustive example of a test article is an ultrasound probe. Another non-limiting, non-exhaustive example of a test article has at least one substantially cylindrical surface. Yet one more non-limiting, non-exhaustive example of a test article is substantially devoid of fissures, cracks, and occlusions.

The term "test pathogen" refers to an agent, such as a disease-producing agent, that is to be deposited onto a test article; said test article for testing against the disinfection or sterilization efficacy of electromagnetic radiation or one or more other disinfection or sterilization processes. Examples of test pathogens, include, but are not limited to, viruses, bacteria, fungi, yeast-molds, spores, chemotherapeutic agents, chemo-toxic agents, chemicals, other toxic material, or other substances that are expected to have some sort of bioactivity.

The test pathogen may in some cases be suspended in a liquid, a gel, or some other suspension agent or concoction to form a test-pathogen mixture. In some cases, the suspension agent is a water based suspension agent, which may be 90-95% by mass of the test-pathogen mixture. In some cases, the bacteria, virus, fungal spores, mold/yeasts, or other pathogens are less than or about equal to one percent (1%) by mass of the test-pathogen mixture's mass. In other cases, the test pathogen may have a different concentration.

Other elements may also be present in the test-pathogen mixture such as pH controlling or buffering agents, dispersants, stabilizers, or other elements that provide benefit to the test-pathogen mixture. In some cases, elements are included in the test-pathogen mixture to increase its stability, dispersion, suspension, homogeneity, or other physical or chemical properties. In some cases, interfering elements may be included in the test-pathogen mixture to simulate potential effects of native biological materials on the efficacy of the disinfecting agent or process. A non-limiting, non-exhaustive list of these elements includes Bovine/Human Serum Albumin (BSA/HSA), Fetal Calf Serum (FCS), and metal salts (e.g., potassium, sodium, calcium, magnesium salts, and the like). The inclusion or exclusion of any of these other non-pathogen elements is not discussed in detail in the present disclosure.

The term "test-pathogen mixture" refers to a sample that is to be deposited onto at least one reference surface of a test article. The test-pathogen mixture may include the test pathogen itself or a combination of the test pathogen along with other liquids or matter as described herein. For example, the test-pathogen mixture may be a suspension, solution, concoction, or other combination of the test pathogen with other liquids, solids, gasses, gels, or other materials. In some embodiments, the terms test pathogen and test-pathogen mixture may be used interchangeably, unless the context clearly dictates otherwise.

The act of depositing the test-pathogen mixture onto the test article may also be referred to as "inoculating the surface with inoculant." In these and other cases, the term "spiking" may also be used. In this context, spiking connotes adding one or more specified elements to an existing mixture, which is in many cases a liquid.

It is an objective in some embodiments to apply on the order of $10^7$ (i.e., 7 LOG) test pathogen per eight square centimeters (8 cm$^2$) of treated area of a test article. In some cases, treated areas (i.e., reference areas) of one or more test articles range from about four square centimeters (4 cm$^2$) to about 12 square centimeters (12 cm$^2$) or more. In some embodiments, the concentration of the test pathogen can be adjusted depending on total volume of suspension material to be deposited. For example, a micro-droplet size of a selected volume can be mathematically combined (e.g., multiplied) by a number of micro-droplets to be deposited. In some cases, a 75 to 100 microliter (µl) volume of test-pathogen mixture is deposited onto an 8 cm$^2$ reference area as about 100 drops; each drop having a volume of 0.75 to 1.0 µl. In these and other embodiments, the test-pathogen mixture may have a test pathogen concentration of between 1.5e8 and 5.0e8 colony forming units per milliliter (CFU/ml). Thus, in these and other embodiments, about 100 droplets can result in 1.3 to 2.7e6 CFU per test article.

Certain High Level Disinfection (HLD) processes demonstrate a 6 LOG reduction of test pathogen. Accordingly, an acceptably produced test article will be formed with about 1.5 times to 10 times that amount of pathogen. In one case carried out in a test environment, 840 droplets, or "dots," were dispensed over a test area of 8 cm$^2$. In this test case, each dot was formed to a volume of about 0.075 µl (i.e., 75 nanoliters (nl)) for a total dispensed volume of 63 µl of suspension, distributed evenly in a staggered pattern over the 8 cm$^2$ test area. The starting suspension had about 1.0e8 CFU/ml, which included about 6.3e6 viable pathogens that were distributed over the 8 cm$^2$ test area, thereby resulting in about 8.5e7 per cm$^2$ of pathogen distributed over the 8 cm$^2$ test area. Other test pathogen concentrations are of course contemplated.

"Wetting" the target area includes the concept of a just-deposited test-mixture drop spreading across its local piece of surface area to an acceptably sufficient degree. In the embodiments described herein, it is desired that test pathogen droplets are distributed evenly across a majority of, or even the entire reference area of, the test article surface such that the reference area of the test article surface is substantially wetted by the test-mixture. Concentrating pathogen is small areas and not making use of a substantial portion of, or in a limiting case the entirety of, the reference area is often not desirable. Such concentration does not emulate in vivo conditions where a medical device might have been contaminated while in use, because a medical device contaminated in actual use typically does not exhibit extraordinarily high or grossly discontinuous local area concentrations of pathogen. Instead, when a medical device contaminated in actual use, the pathogen tends to be more smoothly distributed or "smeared" across a surface, and generally not so highly locally concentrated. Accordingly, it is undesirable to create test articles that do not reflect contact of a medical device with a contaminated surface. In some cases, it is desired that test pathogen concentration be reasonably uniform. In some cases, it is desired that test pathogen concentration be reasonably low so that the total pathogen loading or area count density (ACD) across the treated surface is reduced and is reasonably spatially homogenous. In many of these cases, adjacent droplets of test-pathogen mixture are preferably not touching or joined together. It has been recognized that distributed, uniform pathogen density better emulates endogenous real world contamination, and also better emulates the conventional procedures that produce an even distribution of pathogen on the surface of fully immersed penicylinders as described herein. Such uniform pathogen density also has the added benefit of better emulating a conventional procedure that results in a more even distribution of pathogen on or across the surface of a penicylinder that has been fully immersed in an inoculation broth or suspension as described herein.

With respect to penicylinders, for example, the penicylinders described herein have an approximate surface area of about five square centimeters (5 cm$^2$), which includes the complete penicylinder, inside and out. When conventionally used as described herein (i.e., when the penicylinder is "dunked"), the surface of the penicylinder is fully or at least substantially homogenously covered by pathogen contained in the suspension. Thus the entire surface of the penicylinder is substantially completely inoculated with pathogen. In view of the surface area coverage of a penicylinder, at least some test article embodiments described herein are formed to dimensions of about 2 cm×6 cm. In these cases, a reference area about 6 cm$^2$ to 8 cm$^2$ of the subject test article is inoculated. In at least some embodiments, the inoculated area (i.e., about 6 cm$^2$ to 8 cm$^2$ of the subject test article) is an area of the test article that will later be exposed to a disinfection modality such as ultraviolet light (e.g., UVC). In at least some of these cases, the inoculated reference area is less than all of the surface area of the test article, and in at least some of these cases, an upper portion of the test article where there is a hole from which the test article hangs is not inoculated. In some cases, a perimeter margin (e.g., about 2 mm) of the test article is not inoculated, so the inoculated reference area region is inboard.

Avoiding a recombination (i.e., "bleeding") of adjacent droplets into a single drop that then dries and increases the local ACD is desirable. Bleeding may be considered to be the intentional or unintentional act where one or more liquid fronts advances, wicks, or otherwise travels along a surface away from its intended boundary. In some cases, bleeding includes one liquid traveling and merging into another liquid, which may or may not be traveling. Significant testing has been performed that includes dispensing a test-mixture onto certain carrier surfaces, hydrophobic surfaces in particular. In these cases, it has been recognized that when low viscosity fluids such as water-based solutions, suspensions, and mixtures are dispensed, the dispensed test-mixture forms a roughly hemispherical droplet on the reference area surface rather than uniformly flattening to completely wet the reference area surface. The bias toward forming the roughly hemispherical droplet substantially depends on the surface energy and resulting contact angle of the droplet's air-liquid interface where the droplet comes in contact with the solid surface of the test article in the reference area. It has also been recognized that low viscosity fluids will tend to wet measurably more on clean glass surfaces, resulting in a larger wetted diameter of the droplet and a less hemispherical sessile droplet. Hence, depending on surface properties and suspension fluid behavior, particular spacing between individual test pathogen deposits may be selectively greater to ensure no "bleed over" to an adjacent deposition site, and a selected drying time may be utilized between adjacent deposits, so that a droplet deposited previously is allowed to dry before another is placed adjacent.

In the embodiments described herein, suspended test pathogens will distribute throughout the suspending liquid phase with substantial homogeneity and not settle or cream as their density is very close to that of the liquid phase. The pathogen will not floc together, assemble, or adhere in any great amount to inner surfaces of a dispensing mechanism such that the suspension concentration changes meaningfully during dispensing. Thus, in some embodiments, no stirring or agitation is performed once the test pathogen is prepared for deposition over a "reasonable" amount of time, which in some cases is less than or equal to about 60 minutes. Nevertheless, in some other embodiments, a test pathogen reservoir may be agitated or mixed periodically during one or more methods of deposition.

Experience with drying micro-droplets of suspension has shown that the test pathogen commonly tends to move toward the air-liquid interface of the drying micro-droplet. This effect may be caused by the test pathogen being "caught" by the shrinking/contracting wall of the droplet as the liquid therein evaporates during drying. The exact area-density distribution of pathogen that results after depositing from various suspensions (e.g., aqueous solutions) on different surfaces has not been exhaustively studied; however, initial observations and initial approximations for this disclosure assume that the ACD (i.e., the number of pathogens per unit area) remains acceptably consistent when considering the entirety of the treated area, and as the micro droplets shrink as they dry. The concentration may be affected or even strongly affected by the actual shape of the drying "puddle" of test-pathogen mixture, and so it is desirable to deposit micro-droplets, or other test-pathogen mixture shapes, having consistent size and shape to reduce possible migration of test pathogen within the micro-droplet. Such migration may be caused by convection and other concentration gradient and diffusion related forces that can result as the suspension agent (e.g., water) evaporates. It is contemplated that the local ACD of an outer ring of test-pathogen residue post-drying may be higher or lower than that in the center of the test-pathogen residue. By making the dots sufficiently small in some cases and depositing them close together, the effect of very large dots forming thick, separate and distinct layers of test-pathogen residue is avoided.

A set of test data is presented in Table 1. In Table 1, a first column represents a particular volume droplet of a test-pathogen sample. A second column approximates a droplet, or "dot," diameter. A third column sets forth a test orifice tip gauge of a test-pathogen dispenser embodiment, and a fourth column approximates a number of droplets that are dispensed to achieve a 10 μl dose of the test-pathogen mixture.

TABLE 1

Test Data to Deliver a 10 μl Test-Pathogen Dose

| micro-liters | Resulting "dot" diameter in mm (approx.) | Tip gauge (hypodermic) | Droplets required to deposit a 10 μl "dose" |
|---|---|---|---|
| 1.0 | 1.56 | 15 | 10 |
| 0.5 | 1.24 | 18 | 20 |
| 0.10 | 0.73 | 22 | 100 |
| 0.025 | 0.46 | 25 | 400 |
| 0.010 | 0.34 | 27 | 1000 |
| 0.005 | 0.27 | 30 | 2000 |
| 0.00089 | 0.15 | 32 | 11,200 |

In at least one embodiment, a desired number of droplets per test article having a reference area of two centimeters by four centimeters, which is about eight total square centimeters (8 cm$^2$), is between 200 and 1000. In some embodiments, the droplet deposition density is at least 50 droplets per square centimeter. One or more physical or operational limitations of an automated test-pathogen deposition system may determine how many droplets may be applied in a particular unit area. For example, if an automated test-pathogen deposition system has a minimum addressable pitch of 200 microns, then up to approximately 5 drops/mm can be deposited along a line of a particular 8 cm$^2$ test article. In this circumstance, a total of 5×40=200 droplets may be deposited along a given line. Stepping between adjacent lines at the same 5 lines per mm, a total of about 20×200=4,000 droplets. If a one millimeter boundary is placed on the test article, then the total number of droplets may be reduced to about 3,420. In other cases, an automated test-pathogen deposition system has a different addressable pitch of 500 microns, 750 microns, or some other dimension.

In some cases, an interference agent may be added to the test-pathogen mixture to simulate the presence of human proteins in situ, which may make disinfection more difficult. Frequently in such cases, the interference agent mass is less than or about equal to five percent (5%) by mass of the test-pathogen mixture's mass. One such interference agent recommended by U.S. and European authorities is Human Serum Albumin (HSA). Another such interference agent is Simulated Vaginal Fluid (SVF). Other interference agents are also contemplated. The interference agent may be arranged in an actual or mock suspension in water. No simulated pathogen is necessary in some cases, as the interference agent is present in a very small amount that does not affect the mixture's physical properties in a meaningful way.

In some cases, the viscosity of the test-pathogen mixture will be close to the viscosity of distilled water or slightly greater; for example up to 10% greater.

The test-pathogen mixture will generally present no additional mechanical wear risk to any valve or other moving part in the fluid path of the test-pathogen deposition system embodiments disclosed herein. Particular cleaning procedures may be employed to remove any pathogen, interference agent, surfactant, detergent, or other material that adheres to a non-disposable part or portion (e.g., valve, tube wall, reservoir, or the like) of the fluid path. The particular cleaning procedures may include heat, chemical, electromagnetic, or other sterilization means. The particular cleaning procedures may be changed or enhanced when test-pathogen mixtures containing different pathogens are applied in separate operating runs of the test-pathogen deposition system embodiments disclosed herein, which reduces the likelihood of cross contamination. In at least some embodiments, cleaning and the related risk of contamination is obviated by using wetted components that may be discarded after a single use. For example, any one or more of a disposable reservoir, dispensing needle/cannula set, and associated fluid-path elements such as tubing or valve elements may be implemented.

The term "test-pathogen pattern" refers to a substantially uniform distribution of the test pathogen or test-pathogen mixture on the test article. For example, a test-pathogen pattern may be, but is not limited to, an array, a plurality of substantially concentric circles, a sheet, a line, a plurality of lines, a plurality of individual droplets, a plurality of layers, a matrix, a random distribution within a specified and defined area, a continuous film across a determined portion (e.g., a determined length and a determined width of a defined thickness, before, after, or before and after drying) of the reference area, or the like. A substantially uniform distribution may be understood in the context of two or more areas of a test article having a same size, same shape, same surface type, and/or some other characteristic of sameness. When the plurality of two or more areas are treated with a test pathogen or test-pathogen mixture, the volume, spacing, residual pathogen mass that remains post drying, and/or some other characteristic of test pathogen distribution in one of the two or more areas of the test article is within 75%, 85%, 95% or some greater percent of a different one of the two or more areas of the test article.

The present invention may be understood more readily by reference to the following detailed description of the preferred embodiments of the invention. It is to be understood that the terminology used herein is for the purpose of describing specific embodiments only and is not intended to be limiting. It is further to be understood that unless specifically defined herein, the terminology used herein is to be given its traditional meaning as known in the relevant art.

Figure 1B:
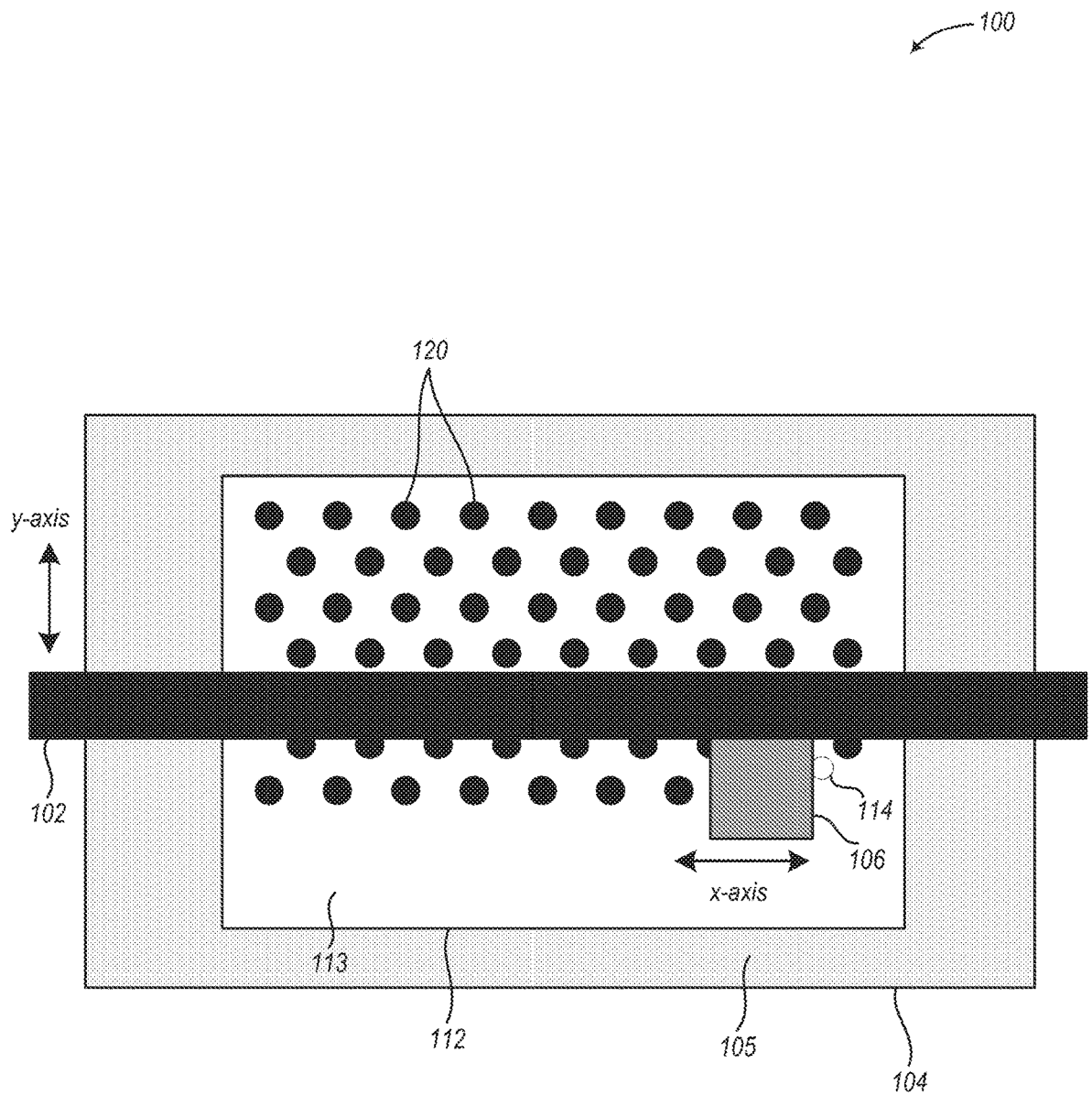
Figure 1C:
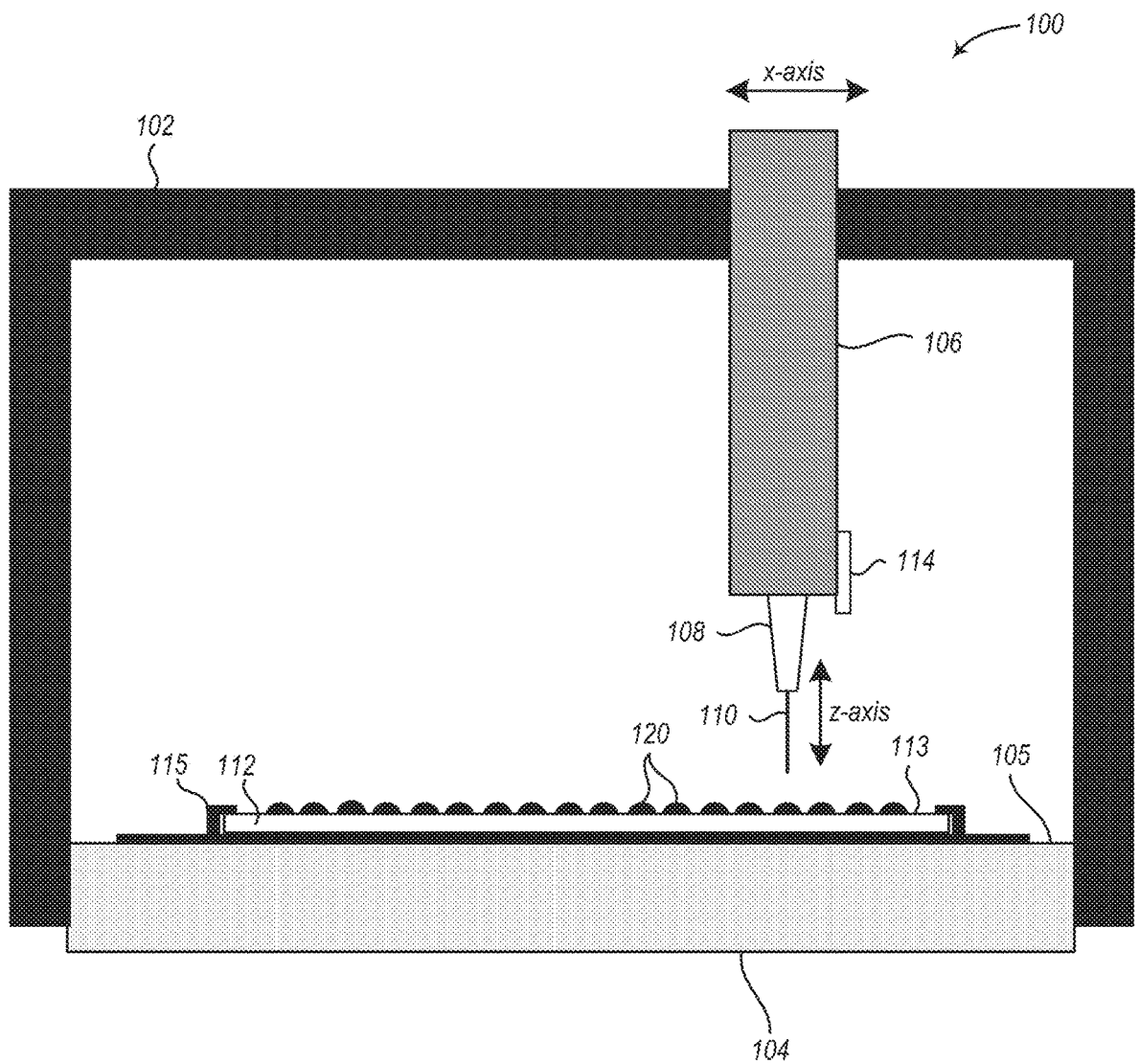
Figure 1D:
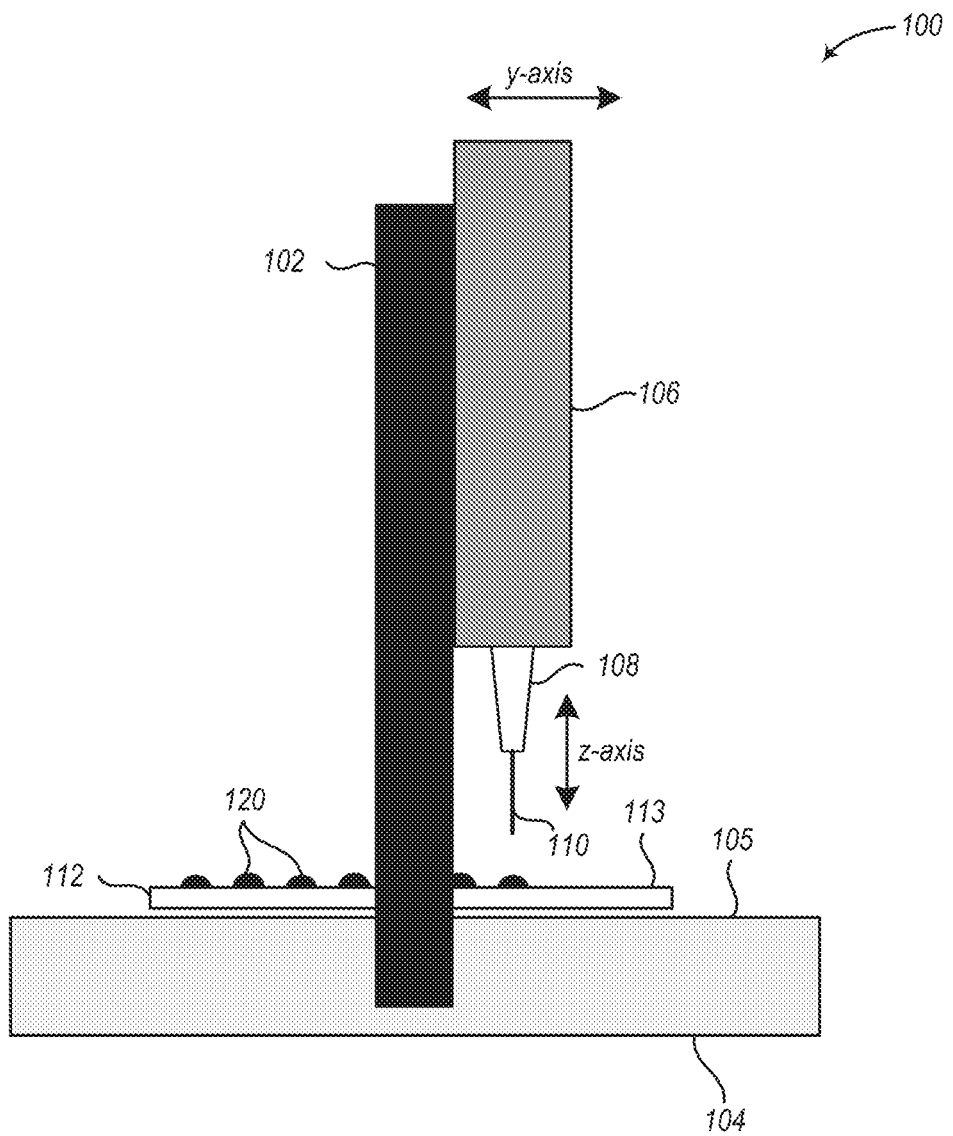

FIGS. 1A-1D show various views of an illustrative example of an automated test-pathogen deposition system 100. FIG. 1A shows a perspective view of an illustrative example of an automated test-pathogen deposition system 100. FIGS. 1B, 1C, and 1D show a top view, front view, and side view, respectively, of the illustrative example of the automated test-pathogen deposition system 100 shown in FIG. 1A.

The system 100 includes a base 104, a gantry 102, and a test-pathogen dispenser 106. The test-pathogen dispenser 106 is structured and moveably connected to the gantry 102 to enable the test-pathogen dispenser 106 to move horizontally in an x-axis direction and vertically in a z-axis direction relative to a top surface 105 of the base 104. The gantry 102 is structured and moveably connected to the base 104 to enable the gantry 102 and the test-pathogen dispenser 106 to move horizontally in a y-axis relative to the top surface 105 of base 104.

The base 104 is structured to include a holding mechanism 115, which in FIGS. 1A-1D is arranged on the top surface 105 of the base 104. In other embodiments, the holding mechanism 115 may be arranged in a different location or orientation. The holding mechanism 115 is structured to removably secure a test article 112 to a portion of the system 100 such as the base 104 while maintaining a reference surface 113 of the test article 112 in a position to receive a test-pathogen mixture from the test-pathogen dispenser 106. Although FIGS. 1A-1D illustrate the holding mechanism 115 as holding a single test article 112, embodiments are not so limited, and in other embodiments, the holding mechanism 115 may be structured to removably secure a plurality of joined or separate and distinct test articles.

The test-pathogen dispenser 106 is structured to deposit a test pathogen in a test-pathogen pattern on the reference surface 113 of the test article 112, which provides a uniform and repeatable distribution of a test-pathogen mixture across the reference surface 113. The system 100 deposits a known or otherwise defined amount of test-pathogen mixture of a known concentration or volume population of a test-pathogen species. As mentioned herein, the test pathogen may be suspended or otherwise combined in a liquid buffer solution, mixture or some other concoction (e.g., an aqueous-based liquid). In at least one such embodiment, the test pathogen comprises 5% or less of the test-pathogen mixture, wherein traceable amounts of the test pathogen are greater than 0%. In some embodiments, the test-pathogen mixture may be specified according to at least one official Association of Official Analytical Chemists (AOAC) International method. In some embodiments, the test-pathogen mixture may also include other buffers, minerals such as metallic salts, and biological material such as albumin (e.g., human albumin or bovine albumin), mucus, blood serum, fetal calf serum, and other biological substances (e.g., proteins, peptides, or enzymes) that may act as to simulate in vivo conditions, to enhance or interfere with the condition of the pathogen or its susceptibility to electromagnetic radiation (EMR), or by simply blocking some of the EMR.

In some embodiments, the test-pathogen dispenser 106 includes a suspension reservoir 108 and a dispenser tip 110. The suspension reservoir 108 is structured to store or control the flow of the test-pathogen mixture from the test-pathogen dispenser 106 to the dispenser tip 110 and onto the reference surface 113 of the test article 112. Typical suspension reservoir 108 volumes may be three cubic centimeters (3 cc), five cubic centimeters (5 cc), 10 cc, 30 cc, or some other volume. In cases where a nominal 10 µl total volume of test-pathogen mixture is deposited per test article 112, a total of one milliliter (1 ml), which is one cubic centimeter (1 cc), is consumed in the treatment of 100 test articles 112. To reduce an effect of changes in air volume-pressure (e.g., in gravity-fed systems) across an operational run to inoculate a plurality of test articles 112, a larger volume reservoir may be selected and loaded with significantly more test-pathogen mixture than will be consumed.

The dispenser tip 110 is structured to deliver the test-pathogen mixture (e.g., the inoculating fluid suspension of test pathogens) to the reference surface 113. Depending on the application of the test-pathogen mixture onto the test article 112 and test-pathogen pattern selected, the dispenser tip 110 may be a liquid-fed roller (e.g., a roller having a cavity to store a determined volume of the test-pathogen mixture and at least one orifice from which to deposit the test-pathogen mixture), liquid-fed or loaded brush (e.g., a capillary-fed delivery system), pressure-fed slot or orifice, liquid loaded screen-print, cannula, needle, or some other fluid transport and deposition mechanism. In at least one embodiment, the dispenser tip 110 may have a conical shape, substantially cylindrical shape, substantially cannular shape, or some other shape that has an exit orifice for the test-pathogen mixture to be deposited onto the reference surface 113 with an inside diameter of approximately 0.05-1.0 millimeters. In at least one other embodiment, the dispenser is arranged as a "print pad," which is a flexibly compliant surface (e.g., silicone) etched with a selected image pattern. In this case, the print pad is first treated with an a test-pathogen mixture, and then the print pad is brought into communication with (e.g., pressed against) the test article 112 such that the test-pathogen mixture is deposited on the reference surface 113. The compliance of the flexible print pad while administering its test-pathogen suspension payload increases the likelihood of good contact and test-pathogen delivery with even irregular or warped reference surfaces 113.

In other embodiments, the dispenser tip 110 may include a mechanically, digitally, manually, and/or automatically controlled atomizing head such that the test-pathogen dispenser 106 "sprays" the test-pathogen mixture on the reference surface 113 of the test article 112. This type of test-pathogen dispenser 106 may include one or multiple nozzles or other openings that emit liquid (e.g., atomized) pathogen suspension as airborne droplets that traverse some distance from the dispenser tip 110 to the reference surface 113. Such devices may include one or more piezo-electric driven sprayers with single emitters or multi-head arrays or other liquid atomizing mechanisms, such as electro-spray, thermal ink-jet, vibrating mesh atomizers, or pressure wave (e.g., ultrasound) driven elements.

In some embodiments, the test-pathogen dispenser 106 may include a pressure source arranged to pressurize the test-pathogen dispenser 106 in a range of between approximately 0.1-10 PSI (e.g., about 2 PSI in at least one embodiment), which may include pressurizing the suspension reservoir 108 to grow test-pathogen mixture droplets of a given volume at the exit orifice of the dispenser tip 110, as described herein. The pressurization mechanism may be operated in response to a timer, a pressure sensor, or some other pressure control mechanism. Locally, the pressurization system may be arranged to apply high pressures (e.g., up to about 10,000 PSI) in a piezo crystal pump. The pressurization may be carried out using compressed air, nitrogen, or another medium. In at least one embodiment, the test-pathogen dispenser 106 may include a fluid pump (e.g., a mechanical displacement pump such as a piston/syringe, peristaltic device, or another such apparatus) interposed between the suspension reservoir 108 and the dispenser tip 110. In other embodiments, a load cell may be utilized to continuously weigh the test-pathogen dispenser 106 to track the loss of fluid mass as the test-pathogen mixture droplets are deposited onto the reference surface 113. Other techniques, such as electro-fluidic techniques or capacitance measurement systems, may also be used to assess the mass, volume, or other measurable characteristics of the deposited droplets.

In the embodiment of FIG. 1A, the test-pathogen dispenser 106 and suspension reservoir 108 are presented in a non-limiting orientation above the test article 112. Embodiments having other orientations of test-pathogen dispensers 106, suspension reservoirs 108, dispenser tips 110, test articles 112, and other portions of the automated test-pathogen disposition system 100 are contemplated. For example, in one case (not shown), a suspension reservoir is positioned below a test article. In this case, a dispenser tip may be arranged as a liquid-fed roller positioned between the reference area of the test article and the suspension reservoir. In this case, the roller will pass the test-pathogen suspension reservoir, pick up fluid on one side, rotate to another side, and roll into contact with the test article.

In some cases, the dispenser tip 110 may be arranged to cooperate with a valve (not shown). The valve may be structured to cycle at up to 600 Hz and run at low air pressures, from one to six pounds per square inch (1-6 PSI)

for example. In other embodiments, the valve may be structured to operate at higher air pressures, for example up to 100 PSI (e.g., 6.9 bar).

As mentioned above, the test-pathogen dispenser 106 is structured to deposit a controlled amount of the test-pathogen mixture on the reference surface 113 of the test article 112. The test-pathogen dispenser 106 may include a microdroplet dispenser that is configured to introduce a substantially accurate volume of the test-pathogen mixture about the reference surface 113. The deposition of the test-pathogen mixture is performed in a desired pattern. In some embodiments, the test-pathogen dispenser 106 deposits a test-pathogen pattern of one or more continuous lines or beads of the test-pathogen mixture. In other embodiments, the test-pathogen dispenser 106 deposits a plurality of discrete droplets or "dots" 120 of the test-pathogen mixture, where each droplet is deposited separate from an adjacent droplet. The test-pathogen dispenser 106 deposits a known (e.g., fixed) or otherwise selected volume or pathogen density (i.e., population counts per unit area, or Colony Forming Units/unit area, referred to here, for example, as $CFU/mm^2$) of the test-pathogen mixture along each line or at each droplet location. For example, in some embodiments, each droplet may be between approximately 0.001 µl and 0.1 ml, although smaller or larger amounts may also be utilized. The number of CFU contained in a drop can be determined by the concentration, which may be referred to as volume count density (VCD), and the volume dispensed. Although FIGS. 1A-1D illustrate only a single dispenser tip 110, other embodiments may include a plurality of dispenser tips that concurrently deposit multiple droplets or lines of the test-pathogen mixture onto the test article 112.

Figure 2A:
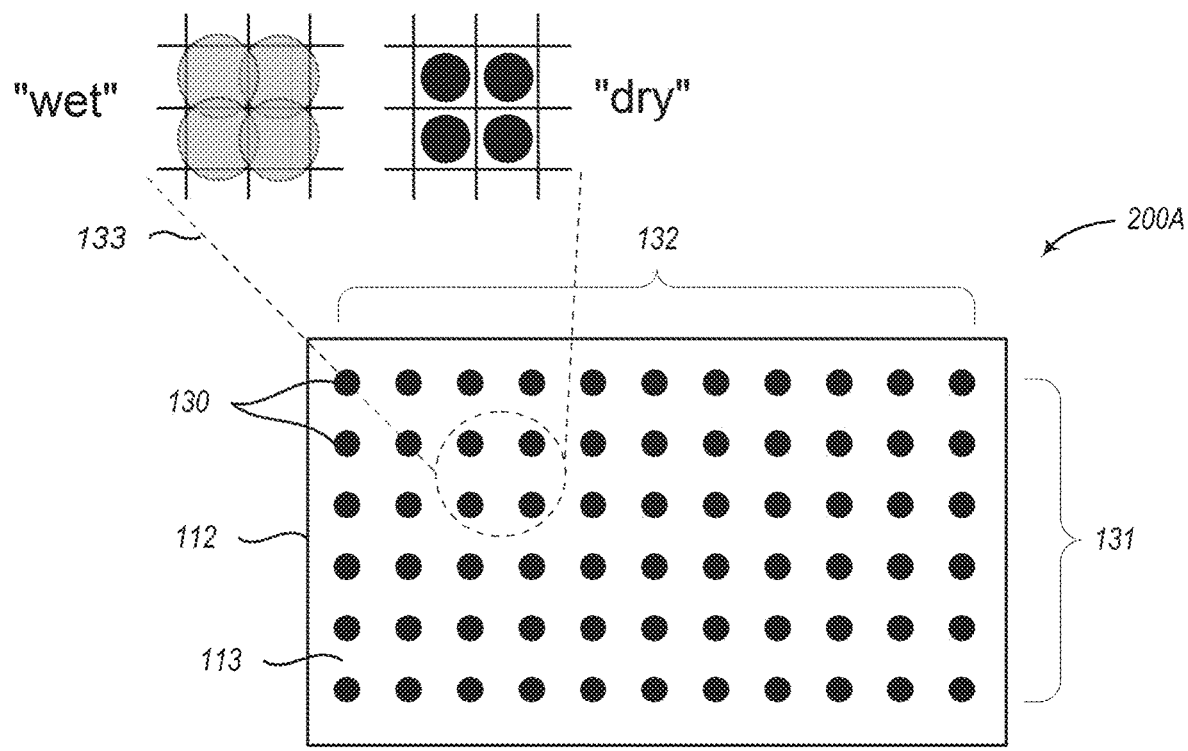
FIGS. 2A-2B show different illustrative examples of a test-pathogen pattern on a test article.
Figure 2B:
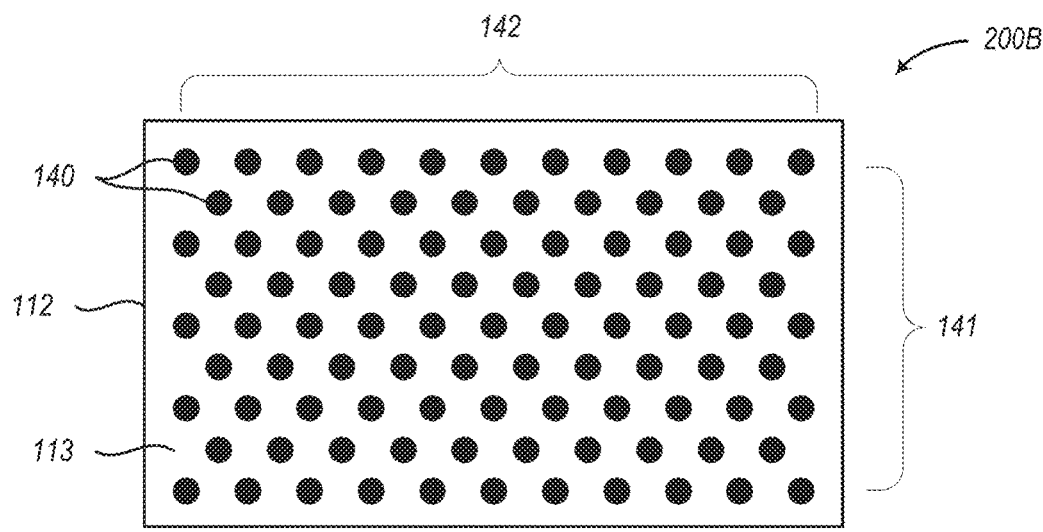
Figure 3A:
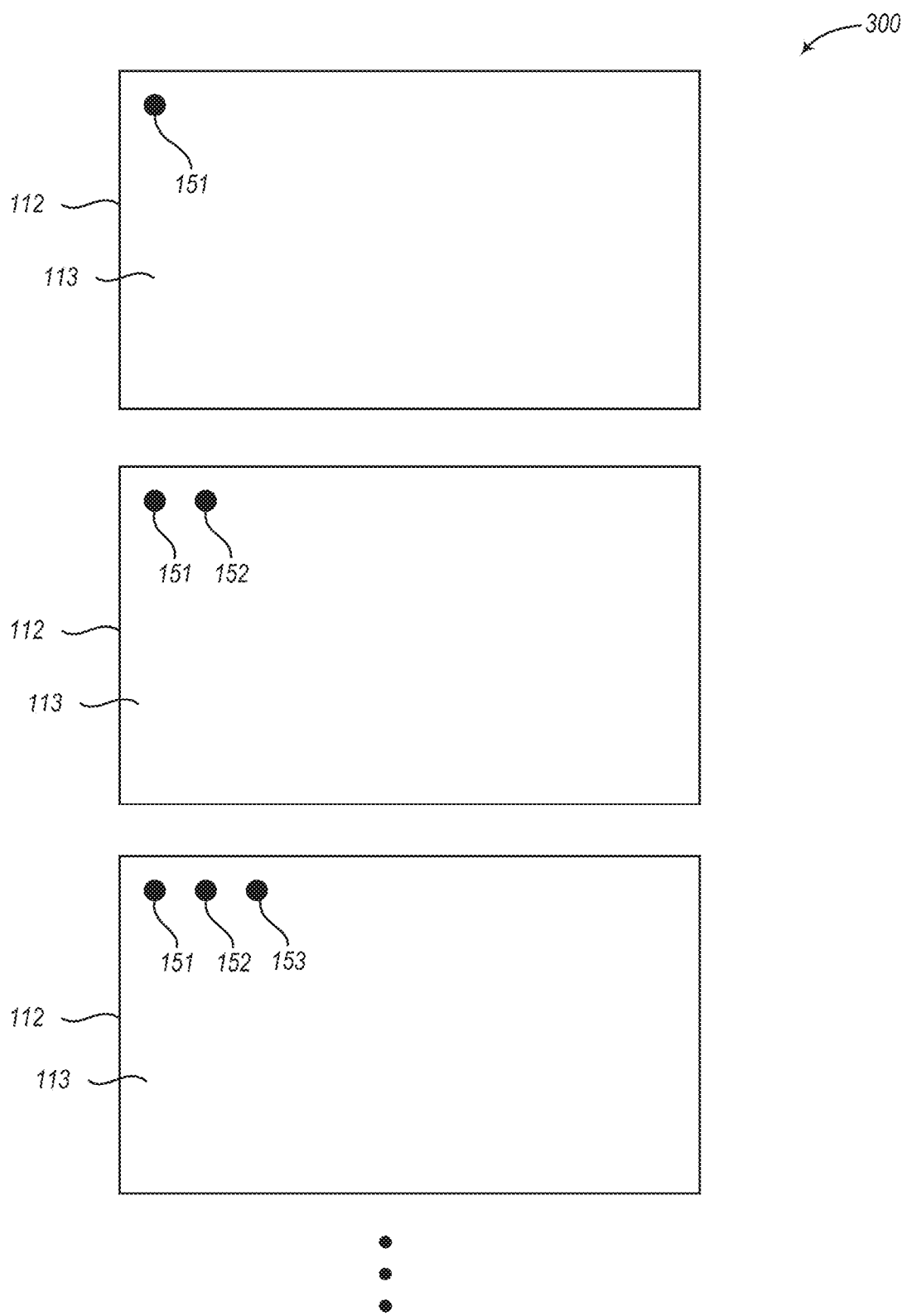
FIGS. 3A-3B show an illustrative example of the sequence of depositing test-pathogen mixture droplets into the test-pathogen pattern.
Figure 3B:
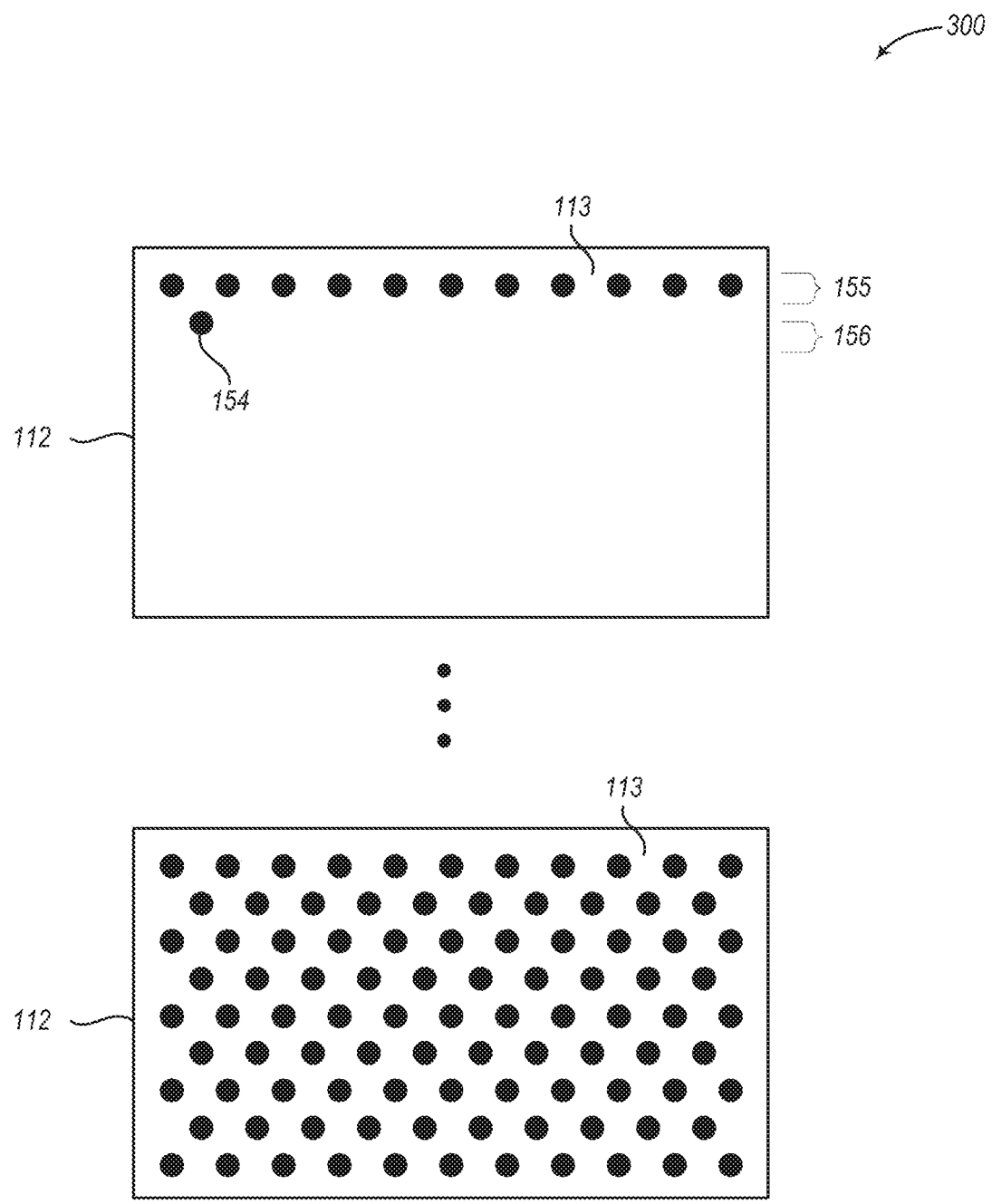

To increase total area covered at a given area count density (ACD) equaling the "dose" distributed across the entire surface, or for other reasons, the test-pathogen pattern of the droplets may include a plurality of rows or columns. In some embodiments, the rows and columns of droplets may be aligned with one another, as illustrated in FIG. 2A. In other embodiments, each row or column may be at least partially offset relative to its respective adjacent row(s) or column(s), such as illustrated in FIG. 2B. It should be understood that other test-pathogen patterns may also be employed. Also, the droplets can be deposited onto the reference surface 113 in a different order depending on the distance between the droplets, the size of each droplet, or other testing parameters. FIGS. 3A-3B and 4A-4B illustrate two non-limiting test-pathogen patterns and the sequence in which each test-pathogen mixture droplet in the pattern is deposited.

Various components of the test-pathogen dispenser 106, suspension reservoir 108, or dispenser tip 110 may be reusable or single use components, depending on the type of test pathogen being tested and acceptable levels or probabilities of cross contamination from the testing of one type of test pathogen to another. For example, in some cases, all or portions of the reservoir 108, pumping system, and/or dispenser tip 110 may be disposable. In some cases, all or portions of the reservoir 108 and/or dispenser tip 110 may be arranged for removal and sterilization or other cleaning. In some cases, the reservoir 108 and/or dispenser tip 110 may include a disposable pumping system and/or a disposable liner, bladder, container, receptacle, or some other repository (not shown), which is disposable.

In some embodiments, the system 100 may also include a sensor 114 (e.g., a range sensor, proximity sensor, force sensor, or another type of distance sensor) to determine the distance between the end of the dispenser tip 110 nearest to the test article 112 and the reference surface 113 of the test article 112. In some embodiments, the sensor 114 may utilize reflected sound or light, or capacitance, or other magneto- or electro-optical devices to determine this distance. In some embodiments, the sensor 114 may also be utilized to confirm that the test-pathogen mixture has been properly deposited onto the reference surface 113. This confirmation may be performed by determining the same distance at the position where the test-pathogen mixture was deposited. If the test-pathogen mixture was properly deposited, then the distance would be less than without the test-pathogen mixture but within a threshold range that is predetermined for an acceptably accurate deposition of the test-pathogen mixture.

It should be understood that the test-pathogen dispenser 106 or the test article 112 translate with respect to each other. As illustrated, the test article 112 may be removably affixed to the base 104, and the gantry 102 and test-pathogen dispenser 106 may move relative to the base 104 and the stationary test article 112. In other embodiments, the test-pathogen dispenser 106 or the gantry 102, or both, may be stationary relative to the base 104, and the base 104 may include a mechanism (not illustrated) that moves the test article 112 relative to the stationary test-pathogen dispenser 106. In yet other embodiments, the system 100 may be structured such that both the test-pathogen dispenser 106 and the test article 112 can move relative to one another.

Moreover, the test-pathogen dispenser 106 may be structured to move in a vertical direction (z-axis) relative to the top surface 105 of the base 104. In this way, the test-pathogen dispenser 106 can move towards and closer to the test article 112 to deposit the test-pathogen mixture on the reference surface 113 of the test article 112, and then move away and further from the test article 112 so that the test-pathogen dispenser 106 is repositionable to another location (e.g., y-axis) about the reference surface without disturbing the previously deposited test-pathogen mixture.

Although FIGS. 1A-1D illustrate the reference surface 113 as being substantially planar or flat, embodiments are not so limited. Rather, the reference surface 113 may be a convex surface, concave surface, planar surface, otherwise shaped surface, irregular surface, or some combination thereof. With these types of curved, multi-structured, or varying contoured reference surfaces, the system 100 may include one, two, or three additional rotational axes so that the test-pathogen dispenser 106 can be properly oriented and aligned with the test article 112 to deposit the test pathogen on the reference surface 113 of the test article 112. The test article may also be translated, rotated, and otherwise manipulated alone or in concert with movements of the pathogen dispenser 106, to accomplish inoculation. In some embodiments, the reference surface may be substantially devoid of fissures, cracks, and occlusions.

The reference surface 113 of the test article 112 may have an area of suitable size to receive an adequate amount of the test-pathogen mixture to test the efficacy of an electromagnetic radiation process that is performed to disinfect or sterilize the test article 112. For example, in some embodiments, the reference area of the reference surface 113 may be approximately 10-25 centimeters long and between two (2) and 10 centimeters wide. In other embodiments, the reference area may be between four (4) and 250 square centimeters. In yet other embodiments, the reference area may be between 10 square millimeters and 20 square centimeters. However, other sizes or shapes (e.g., a disc or a square, the surface of a Petri dish, or a compliant material or membrane) of reference areas may also be employed.

As mentioned above, the system can deposit the test-pathogen mixture onto the test article in virtually any test-pathogen pattern. FIGS. 2A-2B show illustrative examples of two different test-pathogen patterns.

In FIG. 2A, test pattern 200A includes a plurality of test-pathogen mixture droplets 130 in a uniform grid pattern of rows 131 and columns 132 on the reference surface 113 of the test article 112. In this illustrated example, the number of droplets 130 in each column 132 is equal to the total number of rows such that each row 131 and each column 132 are at right angles to one another.

An enlarged portion 133 of FIG. 2A shows one non-limiting embodiment of droplets in a "wet" state and corresponding droplets in a "dry" state. For purposes of a non-limiting example, the reference surface 113 is divided into a grid of equally sized "squares," though any other shape may also be selected, and only four squares are illustrated in the enlarged portion 133 for simplicity. With respect to the grid of squares, each differential element of the entire reference surface 113 (i.e., each square) is inoculated with a droplet of a specified volume (e.g., a volume in the range of 0.01 to 1.0 µl). Each droplet is formed to contain a population of CFUs of a pathogen or pathogen-mixture, including any other elements such as an interfering substance. The liquid (i.e., "wet") phase in the droplet, which in many cases is substantially water, evaporates off, and the resulting approximately circular "dot" (i.e., "dry") remains.

In the enlarged portion 133, it is recognized that the droplet diameter in the "wet" state may be larger than the side length of a target square. Subsequently, as the circular droplet shrinks in size due to evaporation, the pathogen-laced residue gets smaller and is then contained within the boundaries of the differential square element. Such recognition may in some cases lead to a pattern of droplet deposition that is coordinated with a drying rate or time of a given droplet.

In some embodiments of FIG. 2A, the target range of CFU/dot is between about 1.0e02 CFU/dot to 100e03 CFU/dot. In some cases, the automated test-pathogen deposition system 100 is arranged to produce droplets in the target range of 5.0 to 20 CFU/dot. One approach, for example, arranges system 100 to form 7,500 CFU per dot, and to deposit 840 dots across a reference surface of 8 $cm^2$. In this case, the differential square area includes sides of 1.0 mm down to 0.1 mm, or 10-100 per cm, non-interlaced. Typically 1 mm square, or 100×1 $mm^2$ landing spots per $cm^2$ (non-interlaced) would be arranged as 800 squares over an 8 $cm^2$ area.

As illustrated between the patterns of FIGS. 2A and 2B, depositing droplets in an interlacing pattern can increase the dot density. Other patterns may also be chosen to change dot density in other ways. Also, the number of CFU in a given deposited volume can vary. In view of these characteristics, system 100 as contemplated herein is flexibly arranged to permit a wide range of local ACD that is reproducible with acceptable accuracy. The flexibility permits any number of test articles to be created for specific testing use cases, such as how sensitive a particular pathogen is to a particular disinfection procedure. Bacteria may be 100 times larger than viruses, but viruses may be more sensitive to a particular disinfection procedure. Because system 100 is very flexible, droplets may be formed with a wide range of concentrations (e.g., CFU/dot), and in a wide variety of sizes and patterns (e.g., interlaced, non-interlaced, layered, rolled, stripes, and the like).

The test pattern 200B in FIG. 2B includes a plurality of test-pathogen mixture droplets 140 that are in an offset, interlaced pattern of rows 141 and columns 142 on the reference surface 113 of the test article 112. In this illustrated example, each row 141 is offset from its adjacent rows 141 such that the droplets 140 in a given row 141 are not in the same column 142 of the droplets 140 in an adjacent row 141. In this way, droplets 140 are offset from one another, which can enable the droplets 140 to be closer to one another than in the grid pattern illustrated in FIG. 2A.

FIGS. 3A-3B show an illustrative example of the sequence 300 of depositing test-pathogen mixture droplets into the test-pathogen pattern. Employing embodiments described herein, the test-pathogen mixture droplets can be deposited onto the reference surface 113 of the test article 112. In the illustration in FIG. 3A, the sequence 300 starts by depositing test-pathogen mixture droplet 151 onto the reference surface 113. The sequence 300 then proceeds to deposit test-pathogen mixture droplet 152 adjacent to test-pathogen mixture droplet 151 and then deposit test-pathogen mixture droplet 153 adjacent to test-pathogen mixture droplet 152, and so on. As illustrated, a row of discrete sequential droplets is formed on the reference surface 113 of the test article 112. By employing embodiments described herein, droplets can be continuously deposited onto the reference surface 113 at an acceptable rate.

Once a row 155 (FIG. 3B) of test-pathogen mixture droplets has been deposited onto the reference surface 113, the sequence 300 proceeds to begin a new row 156 of test-pathogen mixture droplets by depositing test-pathogen mixture droplet 154 onto the reference surface 113, as illustrated in FIG. 3B. The sequence 300 continues to deposit droplets in a sequential manner for one or more rows until all test-pathogen mixture droplets in the test-pathogen pattern have been deposited onto the reference surface 113 of the test article 112.

The test-pathogen mixture droplets deposited onto the reference surface 113 may be on the order of 0.5 μl or smaller (although other amounts may be utilized). As described above, the droplets may be a suspension of liquid (e.g., water) and the test-pathogen species itself. Due to their size, droplets may be affected by rapid evaporation of the fluid contained therein. After the fluid evaporates, what remains is a film comprising the payload test pathogen and other non-volatile components of the suspension if any. This "residue" is contained within the region of the reference surface that the droplet was originally in contact with.

In order to promote a more homogenous distribution of test-pathogen over the entire reference surface, it may be desirable to prevent one test-pathogen mixture droplet from touching and "bleeding into" another adjacent droplet on the reference surface 113 (FIG. 2A). In some embodiments, this may be achieved by simply increasing the distance between adjacent droplets as they are deposited. In other embodiments, an array of spaced-apart droplets may be deposited first, and then after sufficient time has elapsed (e.g., at least 10 milliseconds, at least 100 milliseconds, at least 500 milliseconds), for example to allow drying and therefore shrinkage or some other desirable evolution of the droplet, the test-pathogen dispenser 106 may return and deposit additional droplets interstitially to the initial array, such as further illustrated in FIGS. 4A-4B. In this way, the homogenous distribution of test pathogen may be formed by a plurality of non-touching arrays of test-pathogen mixture droplets.

FIGS. 4A-4B show another illustrative example of a sequence 400 of depositing test-pathogen mixture droplets into the test-pathogen pattern. In the illustration in FIG. 4A, the sequence 400 starts by depositing test-pathogen mixture droplets 161 and 162 in a row 167 onto the reference surface 113 of the test article 112. The sequence 400 proceeds to deposit additional test-pathogen mixture droplets into row 167 and then into row 168 along the lines of what is described above in conjunction with sequence 300 of FIGS. 3A-3B. However, in this example, sequence 400 spaces the test-pathogen mixture droplets (e.g., test-pathogen mixture droplets 161 and 162) and rows (e.g., rows 167 and 168) further apart during a first series of droplet deposits. In this way, after a selected amount of time (e.g., the time to deposit a first series of rows and columns of test-pathogen mixture droplets), sequence 400 can deposit a second series of test-pathogen mixture droplets in between the previously deposited test-pathogen mixture droplets. For example, test-pathogen mixture droplet 163 is deposited between test-pathogen mixture droplets 161 and 162. Again, sequence 400 proceeds to deposit the intermediate droplets along the lines of what is described above.

Figure 4A:
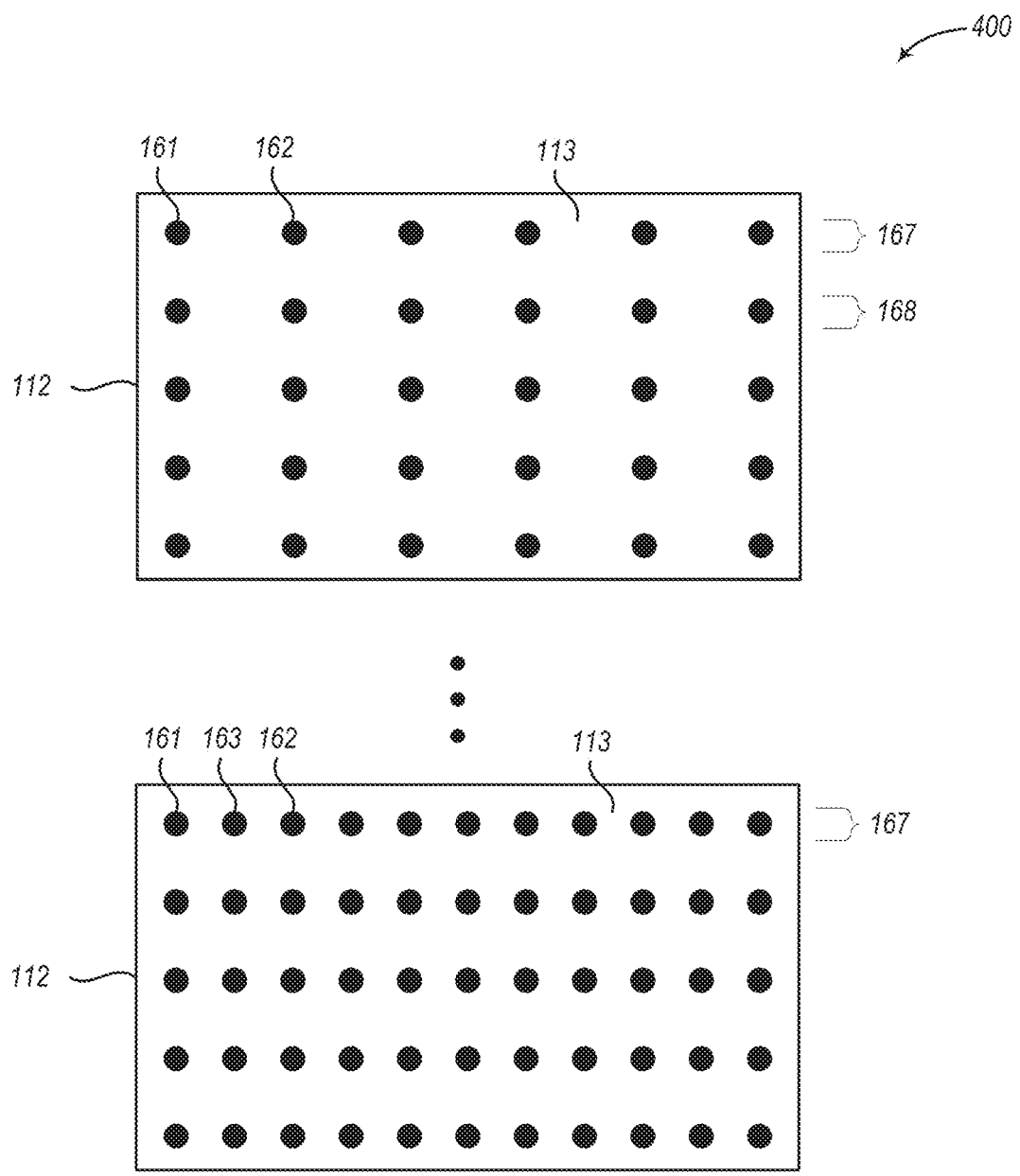
FIGS. 4A-4B show an illustrative example of another sequence of depositing test-pathogen mixture droplets into the test-pathogen pattern.
Figure 4B:
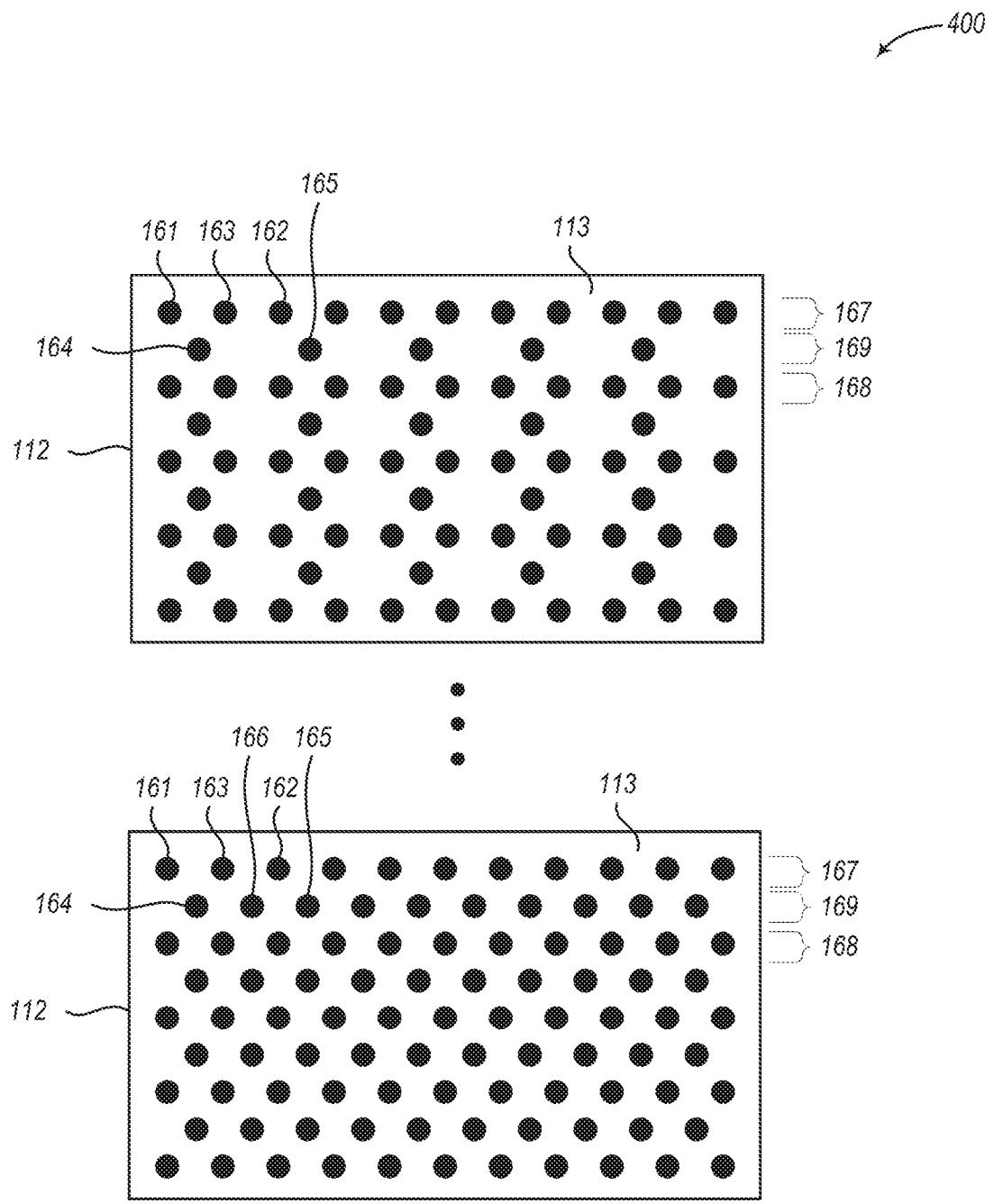

Once a plurality of rows of test-pathogen mixture droplets have been deposited onto the reference surface 113, the sequence 400 proceeds to a third series of droplet deposits by depositing additional rows of droplets in between the previously deposited droplets, as illustrated in FIG. 4B. In this illustration, a row 169 of test-pathogen mixture droplets is deposited between previously deposited rows 167 and 168. In this example, these additional test-pathogen mixture droplets are offset (e.g., substantially equidistant) from the previously deposited test-pathogen mixture droplets. Accordingly, test-pathogen mixture droplet 164 is in row 169 and offset from test-pathogen mixture droplets 161 and 163 in row 167. Again, sequence 400 can skip and not deposit the intermediate test-pathogen mixture droplets during this third series. This is illustrated by there being an absence of a test-pathogen mixture droplet in row 169 between test-pathogen mixture droplets 164 and 165. The sequence 400 can then proceed with a fourth series of droplet deposits to deposit the intermediate droplets that were not deposited in the previously deposited third series of droplet deposits. As illustrated, test-pathogen mixture droplet 166 is deposited between test-pathogen mixture droplets 164 and 165 in row 169 while being offset between test-pathogen mixture droplets 163 and 162 in row 167, which results in a test-pathogen pattern similar to what is illustrated in FIG. 2B.

The shifted array applications of FIGS. 3A-3B and 4A-4B may increase the local area density of test pathogens while reducing bleed over, as the early droplets will have evaporated away from the boundary area and thus be much less likely to combine with the droplets deposited on subsequent passes. Accordingly, one or multiple passes, along with one or multiple dispenser tips, may be utilized to provide an acceptably dense and consistent test-pathogen deposition without bleed over into neighboring sites and while reducing transit time of the test-pathogen dispenser 106 articulating over the reference surface 113 of the test article 112.

In some cases, differently sized or differently constituted droplets may be deposited. For example, in each of the embodiments of FIGS. 2A-2B, 3A-3B, and 4A-4B, discernible space is recognized between individually dispensed droplets. Such spacing is non-limiting, and is illustrated to convey certain features of the systems and methods discussed herein. Nevertheless, it is recognized that additional droplets may be applied to spaces on the reference surface that have not been wetted. These interstitial spaces could be filled with smaller droplets, larger droplets, or the same size droplets to increase packing and overall coverage of the underlying reference surface 113. The different droplets may also have a different concentration, density, or be different in some other way. In some embodiments such as these now described, it may even be permitted that one droplet bleeds over into another adjacent droplet. For example, in one case, four "corner" droplets are deposited in a particular area and permitted to dry. After the four corner droplets have dried, a fifth droplet, which may be larger, smaller, or the same size, is deposited in the space between the four corner droplets. In some cases, bleed over is reduced if the center droplets are deposited after the corner droplets have dried off.

In various embodiments, the system 100 deposits separate, discrete droplets of the test-pathogen mixture onto the test article 112, as described herein. The size of any one or more of these droplets may be controllably varied due to a number of different factors. For example, one controllable factor may be the distance between the dispenser tip 110 of the test-pathogen dispenser 106 and the reference surface 113 of the test article 112. This gap between the dispenser tip 110 and the reference surface 113 is accurately established and maintained during the generation of the test-pathogen pattern, increasing assurance that a controlled or otherwise acceptably known volume of the test-pathogen mixture (e.g., the inoculating liquid suspension that includes the test pathogen) is deposited at each droplet location. Height sensors and position (e.g., servo) controllers may be used to further enhance gap control, and thus further improve accuracy and precision.

Although FIGS. 3A-3B and 4A-4B illustrate two sequences of depositing test-pathogen mixture droplets for a given test-pathogen pattern in accordance with embodiments described herein, other embodiments are not so limited, and other sequences and patterns may be utilized. For example, in some embodiments, the system may continuously deposit one or more lines of test-pathogen mixture in a snake-like or raster pattern on the reference surface of the test article. Such patterns may be determined to permit the desired amount of drying time to elapse such that a residue forms before the dispenser returns to apply another portion of the liquid inoculating mixture.

Moreover, FIGS. 3A-3B and 4A-4B illustrate examples of two sequences that deposit discrete test-pathogen mixture droplets that are independent of one another and not touching or intersecting. Other embodiments are not so limited and, in some embodiments, multiple series or sequences of test-pathogen mixture droplets or lines may be deposited onto the reference surface 113 such that the droplets or lines touch, intersect, overlap, or otherwise create one or more layers of test pathogens.

Figure 5A:
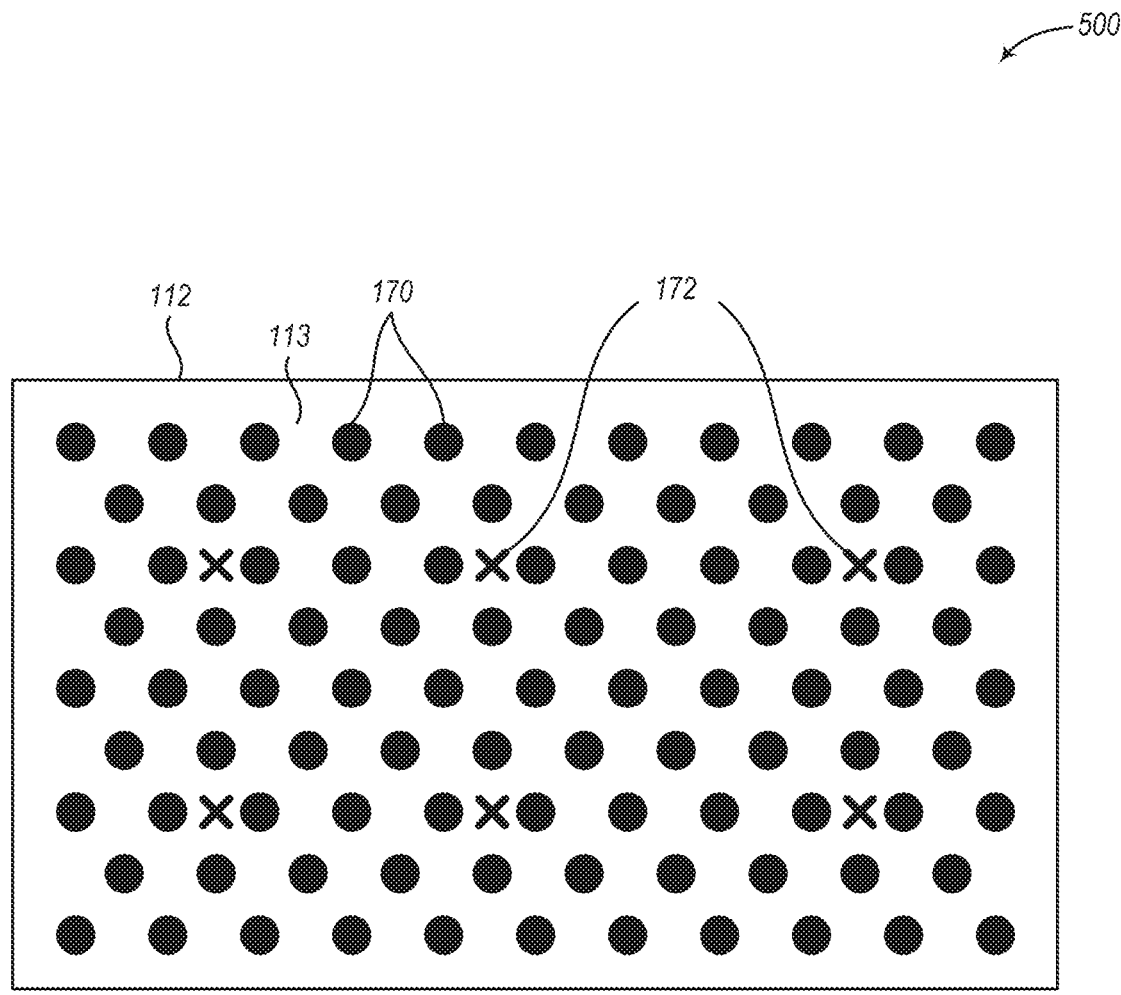
FIG. 5A illustrates a test-pathogen pattern on a test article with distance measurement positions.

FIG. 5A illustrates a test-pathogen pattern 500 of droplets or "dots" 170 on a test article 112 with distance measurement positions 172 therein. The illustrated example includes a plurality of distance measurement positions 172 on the reference surface 113 of the test article 112. In various embodiments, a location of each distance measurement position 172 on the reference surface 113 is predetermined. The distance measurement positions 172 may be equidistant apart from one another or they may be positioned based on other conditions such as changes in the contours of the reference surface 113. Moreover, the system 100 may utilize one or a plurality of distance measurement positions 172 across the reference surface 113. In other embodiments, more or fewer distance measurement positions 172, or different arrangements of distance measurement positions 172, on the reference surface 113, other than what is illustrated in FIG. 5A, may be utilized.

In some embodiments, the distance measurement positions 172 may be vacuum reservoirs, protuberances, or some other structural formation to reduce the likelihood that any test-pathogen mixture or droplet enters the distance measurement positions 172. In other embodiments, the distance measurement positions 172 may be locations where there is a greater distance between test-pathogen mixture droplets, to reduce the possibility of the adjacent test-pathogen mixture droplets from bleeding into one another. In this way, the reference surface 113 maintains one or more pathogen-free areas that can be used as a benchmark location to determine the distance between the reference surface 113 and the dispenser tip 110 of the test-article dispenser 106 at that location. By knowing the distance between the reference surface 113 and the dispenser tip 110, the system 100 can more accurately deposit uniform test-pathogen mixture droplets or lines on the reference surface 113.

In some embodiments, the system 100 may include a force-feedback sensor that detects when the dispenser tip of the test-pathogen dispenser 106 or a droplet formed thereon contacts (e.g., touches) the reference surface 113. Prior to actually depositing any test-pathogen mixture onto the reference surface, the system 100 may first touch or "palpate" various local points (i.e., distance measurement positions 172) around a target area of the reference surface and create a mathematical model of where the surface is, prior to then depositing test-pathogen mixture droplets in that target area. This allows the system 100 to maintain acceptably close control over the gap between the dispenser tip 110 and the reference surface 113 in the target area, which permits an accommodation of surfaces that are locally tilted or non-planar (e.g., curved). The target area may be the entire reference surface 113 or just a portion of the reference surface 113 that is less than the entire reference surface 113. Accordingly, the system 100 may determine one or more different target areas of the reference surface 113 prior to, or during, the deposition of the test-pathogen mixture onto the reference surface 113.

In other embodiments, instead of first palpating, the dispenser tip may be brought into contact with the reference surface during a test-pathogen mixture droplet deposition. The force-feedback sensor detects that the dispenser tip or a droplet formed thereon is touching the reference surface 113, which may be used to terminate the descent of the test-pathogen dispenser 106. The system 100 may then "grow" the test-pathogen mixture droplet on the reference surface 113 as the test-pathogen dispenser 106 is withdrawn and the dispenser tip 110 pulls away from the reference surface 113, which may help to reduce buildup of the test-pathogen mixture on the dispenser tip 110.

In yet other embodiments, non-contact methods of determining the dispenser tip 110 height above the reference surface may be employed. For example, electromagnetic, acoustic, capacitive, light-based, or other telemetry systems or sensors may be utilized to calculate the distance from the respective sensor to the reference surface 113. By predetermining the distance between the sensor and the dispenser tip 110, the distance between the dispenser tip 110 and the reference surface 113 may be determined.

Figure 5B:
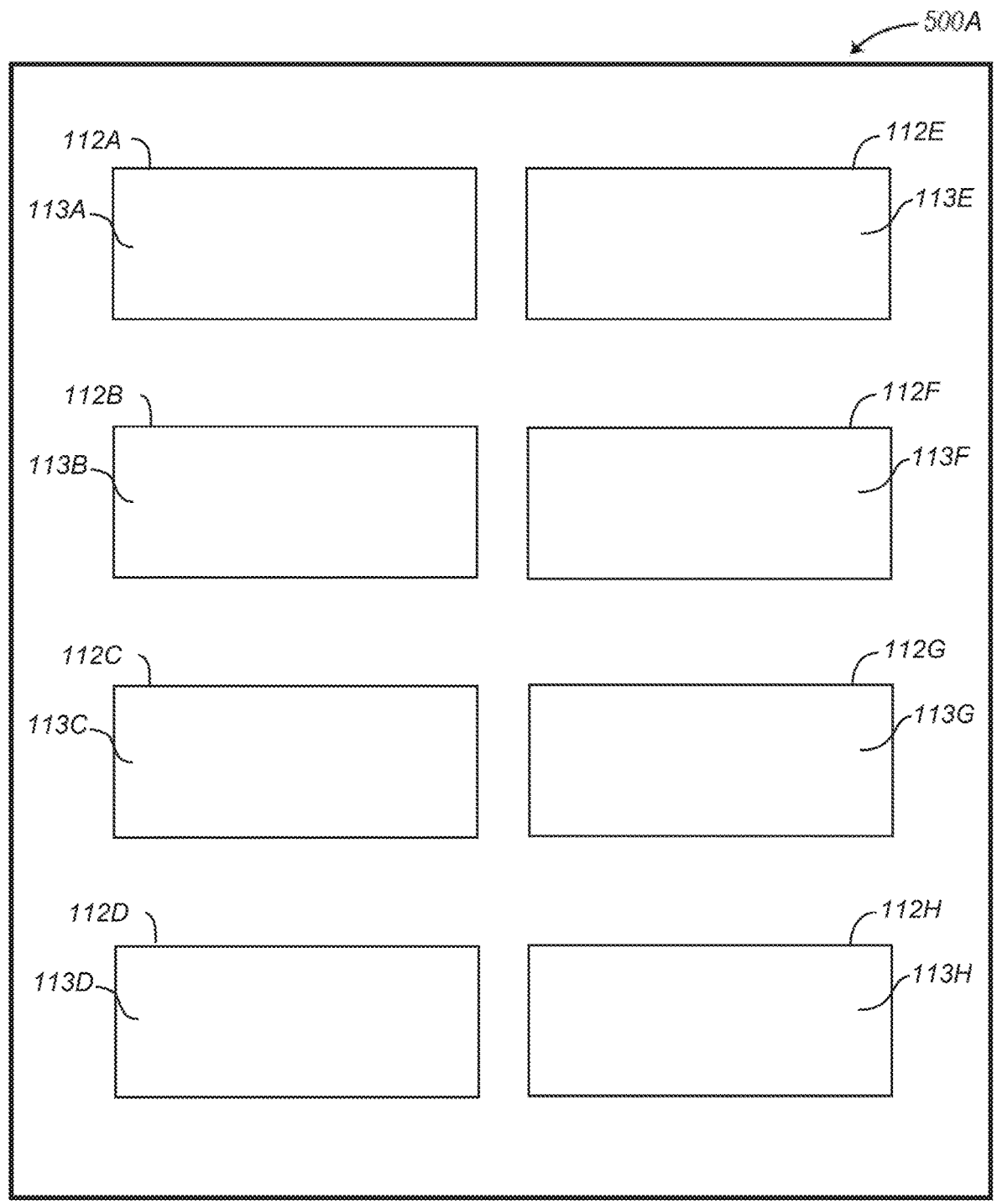
FIG. 5B illustrates a fixture embodiment arranged to removably receive a plurality of test articles.

FIG. 5B illustrates a mounting fixture 500A embodiment arranged to removably receive a plurality of test articles 112A-112H. In some cases, the holding mechanism 115 of the automated test-pathogen deposition system 100 of FIGS. 1A-1D is arranged to removably secure the mounting fixture 500A. In these embodiments, same or different test-pathogen patterns having same or different test-pathogen mixtures may be deposited on the reference surfaces 113A-113H of any one or more of the plurality of test articles 112A-112H.

In the embodiment of FIG. 5B, the mounting fixture 500A has an approximate size of 11 cm by 13 cm. In some cases, the mounting fixture 500A may further be mounted on a platen (not shown) of the automated test-pathogen deposition system 100, In some cases, such a platen has an approximate size of 20 cm by 20 cm. Other sizes of mounting fixtures and platens are contemplated. Other configurations are also configured including, but not limited to, continuously fed belts, horizontally rotating dials, a cylinder along which one or more carriers may be affixed, and other systems that appropriately arrange a test-pathogen dispensing means with one or more test article means.

The test articles 112A-112H of FIG. 5B are illustrated as all having a same or nearly same size, shape, and orientation for ease in understanding. One or more of test articles 112A-112H in other embodiments may have different sizes, shapes, thicknesses, material compositions, orientations, or other characteristics. In the embodiment of FIG. 5B, each test article 112A-112H is rectangular and sized to approximately two centimeters (2 cm) by four centimeters (4 cm) for an approximate area of eight square centimeters (8 cm$^2$).

In the embodiment of FIG. 5B, each test article 112A-112H has a thickness of two millimeters to three millimeters (2-3 mm), and each test article 112A-112H has a similar "flatness," which may vary up to about one half millimeter (0.5 mm) across the surface of a respective test article 112A-112H. In some cases, the variance in flatness between test articles 112A-112H may be caused by cleaning, sterilization, or other processes, which may cause some amount of distortion or warp.

As so arranged, each test article 112A-112H has a respective reference area 113A-113H that begins at about one millimeter (1 mm) inside each edge of the test article 112A-112H. In this configuration, the deposition target region (i.e., reference area 113A-113H) of each test article 112A-112H has test-pathogen mixture deposited in an area one millimeter (1 mm) inside each edge of the test article 112A-112H, for an actual treated area of 1.8 cm×3.8 cm, which is a total area of about 6.84 cm$^2$. This arrangement provides a pathogen-free boundary area around the test articles 112A-112H to allow gripping the respective test article on its sides with a reduced risk of cross contamination.

The test articles 112A-112H may be formed of porcelain ceramic, silicon rubber, Schott-type laboratory glass, stainless steel (e.g., grade 304 commonly), acrylonitrile butadiene styrene (ABS), polybutylene terephthalate (PBT), polycarbonate, nylons, other plastics in use in the medical device industry, or some other material or combination of materials. In the embodiment, only the top surfaces (i.e., reference areas 113A-113H) are treated, and other surfaces of the test articles 112A-112H are not treated. After a test-pathogen mixture is deposited in a test-pathogen pattern on one or more of the test articles 112A-112H, the reference areas 113A-113H are air dried, post deposition.

It may be desirable to increase speed through-put, reduce handling risks, and achieve other benefits when performing test-pathogen mixture deposition processes. The embodiment of FIG. 5B advances these goals by permitting a plurality of test articles 112A-112H to be treated in a same run. In this embodiment, each test article 112A-112H may include one or more locating features (not shown). Locating features may include markings or other like indicia, protuberances, holes, or other features arranged to register a particular location. For example, in some embodiments, a locating feature includes or provides a reference surface such as a tapered "pin" that mates with an angled surface or surfaces. In other embodiments, cooperating locating features bias together a pair of mating surfaces to establish a well-controlled relative position. Other locating features are contemplated. The locating features may be arranged on any one or more of the mounting fixture 500A and test articles 112A-112H.

In some cases, a vacuum structure (not shown) is employed to retain and hold one or more of the mounting fixture 500A and test articles 112A-112H. The vacuum structure may include a HEPA filter. In other embodiments, a different type of structure is arranged to removably affix the one or more of the mounting fixture 500A and test articles 112A-112H to the automated test-pathogen deposition system 100.

In some embodiments, the mounting fixture 500A is arranged for easy and quick connection and disconnection of a mounting fixture 500A from the automated test-pathogen deposition system 100. Such connection or disconnection may be performed by one person or automatically. In some cases, two or more mounting fixtures 500A may be connected or disconnected in just a few seconds or even less.

In some cases, the mounting fixture 500A, a platen, or one or more other structures are arranged for covering by a laminar flow hood, another open or closed containment system, or a disposable or sterilizable shroud (not shown). Such a shroud may be formed of TYVEK, polyethylene sheet, or some other suitable shroud material. The shroud may be used in pathogen-mixture deposition procedures to reduce the likelihood of undesirable contamination of particular areas and structures while also permitting concurrent inoculation of one or more test articles 112A-112H. Such hood, shroud, or other containment system operates to reduce or prevent contamination of test articles, once inoculated, by externally originating pathogens.

Figure 6:
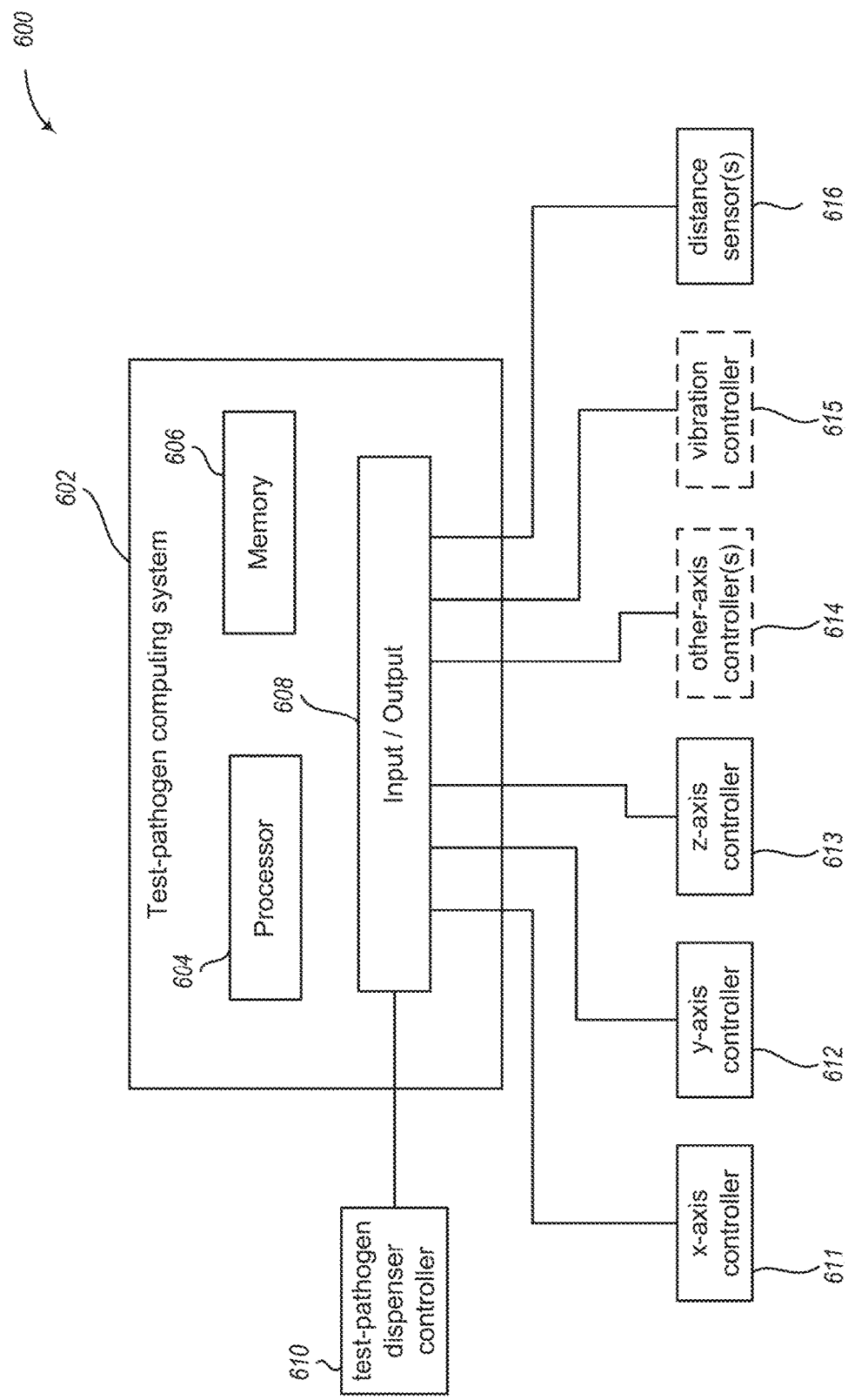
FIG. 6 is a system diagram of a computing system that controls the test-pathogen system to deposit test pathogens onto a test article.

FIG. 6 is a system diagram of a computing system 600 that controls the system 100 to deposit test-pathogen mixture onto a reference surface 113 of a test article 112. The system 600, which may be a part of the test-pathogen deposition system 100, includes a test-pathogen computing system 602, a plurality of controllers 610-615, and one or more optional distance sensors 616.

The test-pathogen computing system 602 includes a processor 604, a memory 606, and an input/output interface 608. The processor 604 includes one or more processing units (e.g., central processing units) that execute instructions to perform actions, including actions to perform embodiments described herein to control the deposition of test pathogens onto a test article 112.

The system 602 is arranged to generate and distribute one or more control signals that move one or more portions of the test-pathogen dispenser 106, the test article 112, or some combination thereof. Along these lines, one or more control signals may also be generated to form, release (e.g., spray, deposit, or the like), or form and release a substantially accurate volume (e.g., quantity, mass, or the like) of the test-pathogen mixture. The control signals may be generated and applied based on mechanical input, electronic input, one or more computer programs, or a combination thereof.

The memory 606 includes one or more types of non-volatile and/or volatile storage technologies. Examples of memory 606 include, but are not limited to, flash memory, hard disk drives, optical drives, solid-state drives, various types of random access memory (RAM), various types of read-only memory (ROM), other transitory and/or non-transitory computer-readable storage media, which may also be referred to as processor-readable storage media, or other memory technologies, or any combination thereof. The memory 606 may be utilized to store information, such as the computer-readable instructions that are executed by the processor 604 and other information, such as, for example, test-pathogen patterns, reference surface contours or one or more data structures to store such information, or other information that is utilized to deposit test pathogens onto a test article 112.

In these or other cases, at least one sensor (e.g., a force-feedback sensor) is arranged to provide data associated with a plurality of three-dimensional locations of contacted points of the reference area. The test-pathogen computing system 602 can generate at least one data structure representing a location of the reference area of the exposed test article 112, at least one data structure representing a shape of the reference area of the exposed test article 112, at least one data structure representing a model of the reference area of the exposed test article 112, or some other representation of the reference area of interest. In this way, the test-pathogen computing system 602 can be operated as a learning mechanism that travels about the reference area, interrogates the reference area, and records data points, which become points of the model. Subsequently, data of the model is used or otherwise applied by the test-pathogen computing system 602 to generate at least one data structure representing a dispensation pattern for the test pathogen based on the recorded data points associated with the reference area, and repeatably position at least one orifice of the test-pathogen dispenser 106.

The input/output interface 608 provides a communication interface between the test-pathogen computing system 602 and a plurality of other components. For example, the test-pathogen computing system 602 provides information to the controllers 610-615 via the input/output interface 608 and receives information from the optional distance sensor(s) 616.

The test-pathogen dispenser controller 610 is utilized to control the formation or release of test-pathogen mixture droplets or lines onto the reference surface 113 of the test article 112. The x-axis controller 611 controls one or more motors, actuators, or other mechanical devices that move the test-pathogen dispenser 106 in an x-axis direction (FIGS. 1A, 1B, 1C) relative to the test article 112. The y-axis controller 612 controls one or more motors, actuators, or other mechanical devices that move the test-pathogen dispenser 106 in a y-axis direction (FIGS. 1A, 1B, 1D) relative to the test article 112. The z-axis controller 613 controls one or more motors, actuators, or other mechanical devices that move the test-pathogen dispenser 106 in a z-axis direction (FIGS. 1A, 1C, 1D) relative to the test article 112.

The optional other-axis controller(s) 614 control one or more motors, actuators, or other mechanical devices that move the test-pathogen dispenser 106 in additional axes relative to the test article 112 to add additional degrees-of-freedom to the rotation and positioning of the test-pathogen dispenser 106. In some embodiments, these other-axis controller(s) 614 may be optional and may not be utilized. In some embodiments, one or more of the x-axis, y-axis, z-axis controllers, and optional other-axis controllers 611-614 may be combined in a single controller architecture. Other deposition systems that use other coordinate system approaches, such as circular or cylindrical, and additional degrees of freedom, such as "multi-axis" approaches that combine translations with rotations and move both a test article and dispenser with respect to an external reference frame and one another, are also contemplated.

As described herein, the test-pathogen dispenser 106, or the test article 112, or a combination thereof may be moved relative to one another. Accordingly, the controllers 611-614 may control movement of the test-pathogen dispenser 106, movement of the test article 112, or a combination thereof.

An optional vibration controller 615 controls one or more motors, actuators, or other mechanical or acoustic devices that force or induce the dispenser tip 110 of the test-pathogen dispenser 106 to vibrate or otherwise perturbate. The vibration or perturbation is arranged to facilitate detachment of a test-pathogen mixture droplet from the dispenser tip 110. In some embodiments, the vibration controller 615 may be optional and may not be utilized. Other types of systems may also be utilized to help detach the test-pathogen mixture droplet from the dispenser tip 110, such as, for example, an electrostatic charge generation device (e.g., to induce an electrostatic charge on the droplet at the opening of the dispenser tip 110), a pump, a heater, an aerator, or some other device.

One or more optional distance sensors 616 may be arranged to detect a distance between the dispenser tip 110 and the reference surface 113 of the test article 112. In some embodiments, these sensors may be non-contact sensors, such as light- or sound-based telemetry sensors and systems. In other embodiments, the sensors may be based on LIDAR, RADAR, electric or magnetic fields, sensing capacitance, inductance, or some other electromagnetic phenomena, to permit assessment of distance or range of motion about a target.

Light-based sensors may include at least one light-emitting source (e.g., a light emitting diode (LED) or a laser emitting visible or non-visible electromagnetic (EM) radiation, etc.) and at least one photo detector to detect reflected light from the light-emitting source. Sound-based or acoustic-based sensors may include at least one audio source and at least one audio detector. In other embodiments, these sensors may include one or more touch-sensitive or force-feedback sensors that react to compression forces when the dispenser tip 110 contacts the reference surface 113.

The test-pathogen computing system 602 utilizes the measurements from the optional distance sensor(s) 616 to determine the distance between the dispenser tip 110 and the reference surface 113, which is then utilized to adjust the deposition of the test-pathogen mixture onto the reference surface 113 via the test-pathogen dispenser controller 610 or to adjust the position of the test-pathogen dispenser 106 via one or more of the axis controllers 611-614. The distance sensor(s) 616 may also be utilized to determine a size, shape, contours, or three-dimensional (3-D) model of an area the reference surface 113 of the test article 112 in which the test-pathogen mixture is to be deposited. For example, the sensors may be utilized as a learning mechanism to traverse the reference area and record data points that become points of the model. In one case, at least one force-feedback sensor is arranged to provide data points associated with a 3-D location of a contacted point of the reference area. These data points can then be used or otherwise applied by the test-pathogen computing system 602 to repeatedly position the dispenser tip 110 of the test-pathogen dispenser 106, as described herein.

The operation of certain aspects of the disclosure will now be described with respect to FIG. 7. In at least one of the various embodiments, process 700 described in conjunction with FIG. 7 may be implemented by or executed on one or more computing devices, such as test-pathogen computing system 602.

Figure 7:
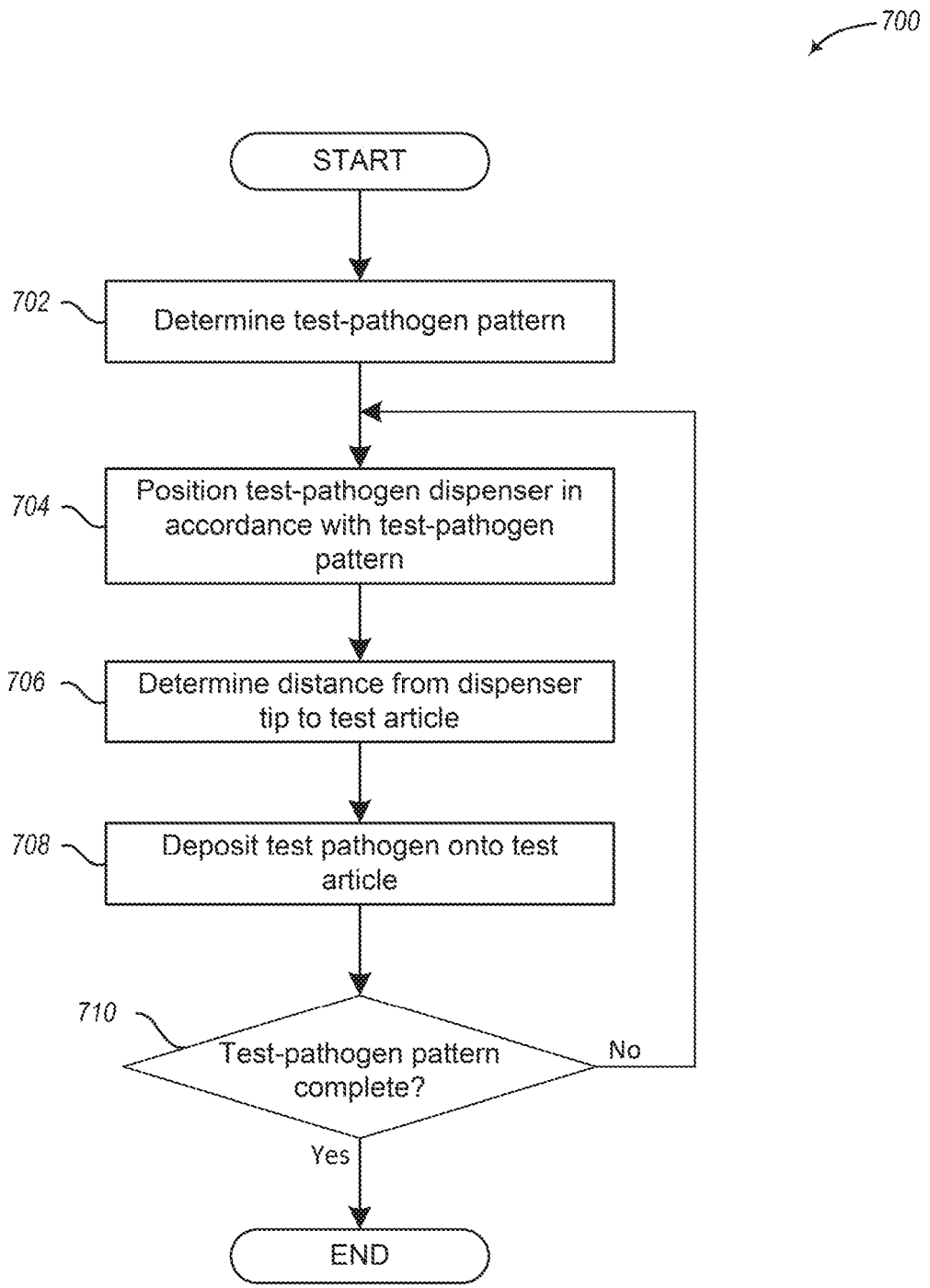
FIG. 7 is a logical flow diagram generally showing one embodiment of a process for depositing the test pathogens onto a test article in test-pathogen pattern.

FIG. 7 is a logical flow diagram generally showing one embodiment of a process 700 for depositing test pathogens onto a test article 112 in a test-pathogen pattern. Process 700 begins after a start block. At block 702 a test-pathogen pattern is determined. In some embodiments, a user inputs the desired test-pathogen pattern. In other embodiments, a test-pathogen pattern may be determined or otherwise selected, such as a previously used test-pathogen pattern. In various embodiments, the test-pathogen pattern may differ, and thus be determined, based on the type of test article 112, the contours of the reference surface 113 of the test article 112, the material of the reference surface 113, the type test pathogen being utilized, or other testing parameters.

Process 700 proceeds to block 704, where the test-pathogen dispenser 106 is positioned in accordance with the test-pathogen pattern. As described herein, the test-pathogen dispenser 106 may systematically deposit one or more test-pathogen lines or droplets at a time in the test-pathogen pattern. Initially, the test-pathogen dispenser 106 is positioned at a first location of the test-pathogen pattern in which to deposit the test-pathogen mixture onto the reference surface 113 of the test article 112.

Process 700 continues at block 706, where a distance from the dispenser tip 110 of the test-pathogen dispenser 106 to the reference surface 113 of the test article 112 is determined. In some embodiments, the contours or a three-dimensional (3-D) model of the reference surface 113, or a test area of the reference surface 113, may be initially determined prior to the positioning of the test-pathogen dispenser 106 at block 704. In one such embodiment, the distance from the dispenser tip 110 to the reference surface may be determined at the current position of the test-pathogen dispenser 106 based on the predetermined contours of the reference surface 113. Here, the use of a vertical z-axis may be employed. In other embodiments, the distance between the dispenser tip 110 and the reference surface 113 may be determined for each location or for a plurality of locations where the test-pathogen mixture is deposited onto the reference surface 113.

Process 700 proceeds to block 708, where the test-pathogen mixture is deposited onto the reference surface 113 of the test article 112. As described herein, the test-pathogen mixture may be applied to the reference surface 113 as one or more lines or one or more droplets. Similarly, one or more test-pathogen lines or droplets may be deposited simultaneously before depositing another set of test-pathogen lines or droplets. Alternatively, a first local region of the test article 112 may be treated, and then a second local region may be treated after the dispenser tip 110 transits to the second local region. In this way, application of the test-pathogen mixture may include many cycles of partial treatment of a plurality of sub-regions, and these multiple cycles may include repeated returns for second, third, and more "coats" (i.e., applications of test-pathogen mixture) to a same region.

In at least one embodiment where test-pathogen mixture droplets are deposited onto the reference surface 113, a fixed, substantially accurate volume of the test-pathogen mixture is issued from and "grown" on the tip of the dispenser tip 110 (e.g., where the dispenser tip 110 is a cannula or needle). In some embodiments, this process of growing the test-pathogen mixture droplet is performed when the test-pathogen dispenser 106 is stationary at the just-deposited site, at the position of the to-be-deposited test-pathogen mixture droplet site, or at some other location. In other embodiments, this process of growing the test-pathogen mixture droplet may begin before or while the test-pathogen dispenser 106 is in motion from its initial position or from the position of one droplet to the next. For example, droplet formation may start while the dispenser tip 110 is still laterally stationary in a prior spot but while the apparatus is retracting along one or more of its axes. Then, the droplet may keep growing as the dispenser tip 110 transits to new location. Droplet formation may finish before the dispenser tip 110 is lowered to touch the reference surface 113. Alternatively, droplet formation may complete its growth while the dispenser tip 110 is in its desired z-axis position such that the droplet is "grown" into the reference surface 113.

In various embodiments, a device may be utilized to supply positive pressure to grow and form a test-pathogen mixture droplet at an orifice of the dispenser tip 110 and to supply negative pressure to hold the test-pathogen mixture droplet at the orifice of the dispenser tip 110.

Because of the small volumes of the test-pathogen mixture droplet, and therefore the small mass of the droplet, fluid surface forces on the droplet may be stronger than the gravitational pull on the droplet. Accordingly, in some embodiments, the test-pathogen mixture droplet may remain in contact with (or "hang from") the tip/orifice of the dispenser tip 110 where it was generated. The test-pathogen dispenser 106 or the dispenser tip 110 may move so that test-pathogen mixture droplet is brought into contact with the reference surface 113. This contact initiates "wetting" forces to act and pull on the droplet, which results in the test-pathogen mixture droplet being separated or otherwise disconnected from the dispenser tip 110 and "touched-off" onto the reference surface 113. In some embodiments, the test-pathogen dispenser 106 or the dispenser tip 110 may be moved away from the reference surface 113 to quickly stretch and "snap-off" the test-pathogen mixture droplet so the droplet becomes free of the dispenser tip 110.

Various other techniques, methods, and mechanisms may be employed to induce the test-pathogen mixture droplet to detach from the dispenser tip 110 and to attach to the reference surface 113. Such techniques may also be configured or otherwise selected to reduce the amount of pathogen-mixture residue that remains on the dispenser tip 110.

For example, in some embodiments, mechanical vibrational energy may be applied to the dispenser tip 110. In other embodiments, the dispenser tip 110 may be treated with polymers or other chemicals having low surface energy with respect to the inoculating fluid of the test-pathogen mixture droplet. In yet other embodiments, the dispenser tip 110 may be designed to reduce its surface area contact with the suspended test-pathogen mixture droplet. In still other cases, a companion device (not shown) may be arranged proximate to the dispenser tip 110 and configured to treat certain target locations in advance of depositing the test-pathogen mixture droplet. In these cases, the companion device may apply a corona discharge or liquid wetting agent, for example, to a particular target surface to temporarily increase hydrophilicity. Each of these other techniques can increase wetting to force or otherwise pull the droplet from the dispenser tip 110, can reduce the surface tension between the test-pathogen mixture droplet and the dispenser tip 110, or can otherwise controllably increase the relative bias of the droplet toward the reference surface 113, which thereby increases the ability of the test-pathogen mixture droplet to attach to the reference surface 113.

In yet other embodiments, the reference surface 113 may be treated with a chemical (e.g., a surfactant, a detergent, or the like) to increase its wetting or adhesion properties and to increase the tension forces between the test-pathogen mixture droplet and the reference surface 113, which also can increase the ability of the test-pathogen mixture droplet to attach to the reference surface 113. In some embodiments, however, non-chemical wetting agents (e.g., corona discharge) may be desirable.

In some embodiments, at least one drying structure is integrated with or otherwise associated with the automated test-pathogen deposition system 100. The drying structure may be integrated with the base 104 of the system 100, the gantry 102, or some other portion. The drying structure may be used to accelerate evaporation of droplets, and thereby increase throughput or achieve other desirable results. The drying structure may include heated or un-heated air that is directed onto, over, past, or in other proximity to the reference surface 113. The drying structure may use ambient, filtered air, or another drying gas. The drying gas may contain another substance, such as a percentage of water, a dissolved vapor of an organic solvent (e.g., ethanol, acetone), or another substance that acts as a drying agent. The air that passes the reference surface 113 may be dehumidified. In some cases, the drying structure may provide heat to a reference surface 113 from below, from above, from any side, or some combination thereof. The heat may be transferred to the reference surface 113 by conduction, convection, or another method. The heat source may be of any desirable technology (e.g., resistive, infrared, and the like). The heat source may direct or otherwise focus heat toward one or more specific regions of the reference surface 113 and not toward other areas. It has been recognized that long wavelength electromagnetic radiation may not be effective to sterilize certain pathogens. In some cases, the drying source includes one or more temperature sensors and control logic to avoid overheating the reference surface, which may degrade the test-pathogen.

As described herein, one example of a dispenser tip 110 may be a dispensing cannula or needle. In some embodiments, the needle may be translated vertically downward to the reference surface 113 (i.e., the dispenser tip 110 may be reciprocating) to deposit each test-pathogen mixture droplet. The dispenser tip 110 may be configured along its z-axis to arrange a desired gap between the dispenser tip 110 and the reference surface 113 such that a droplet may be touched off on the reference surface 113, but also such that the dispenser tip 110 does not physically contact the reference surface 113. In other embodiments, multiple dispenser tips may be structured radially about a central axis similar to spokes on a bicycle wheel, which can rotate about the central axis. This rotation can result in a similar motion of each dispenser tip 110 being moved close to the reference surface so that a respective test-pathogen mixture droplet contacts the reference surface 113, and then this rotation moves each dispenser tip 110 away from the reference surface 113 to detach the respective test-pathogen mixture droplet from the dispenser tip 110. In this manner, each dispenser tip 110 may not perform any reciprocation motion, which can offer improvements in speed or cycle time. In still other embodiments, a plurality of dispenser tips may be formed in a line, an array, or some other cluster.

As described herein, the test-pathogen dispenser 106 or the test article 112, or both may be moved relative to one another. Accordingly, in some other embodiments, the test article 112 may be moved so that the reference surface 113 of the test article 112 is brought toward a fixed dispensing needle.

Process 700 continues at decision block 710, where a determination is made whether the test-pathogen pattern is complete. In some embodiments, this determination is based on whether the test-pathogen mixture has been deposited onto the reference surface at each location identified by the test-pathogen pattern. If the test-pathogen pattern is not complete, then process 700 returns to block 704 to adjust the position of the test-pathogen dispenser to deposit the test-pathogen mixture at another location in the test-pathogen pattern; otherwise, process 700 ends.

The test articles described in the present disclosure may be formed of selected materials and having selected dimensions. In some cases, however, the test articles may also include particular medical devices such as vaginal and rectal ultrasound probes, endo-tracheal probes, and other endo-cavitary (i.e., internal-cavity) ultrasound probes of similar size and construction. These devices may have uniform or non-uniform shapes, dimensions, materials of construction, and other characteristics. The test-pathogen mixtures described herein may be deposited as "dots," rolled or brushed on as a "sheet," applied with a print pad, or applied in other ways. For example, on a vaginal ultrasound probe, which has portions that are round, the automated test-pathogen deposition system 100 may be arranged to dispense a continuous line or a line of droplets that follow a line pattern while the probe is rotating. In such cases, the test article probe or other device will have a rotation that is synchronized with the speed of the test-pathogen dispenser 106.

In some cases, the test articles described herein may have at least one dimension that is 20 to 30 cm long or longer. In these cases, some portion of the test article may extend out from the automated test-pathogen deposition system 100. In some embodiments, a mounting fixture 500A (FIG. 5B) or a platen (not shown) may also be arranged to move in one, two, or three orthogonal directions.

In some cases, the test articles described herein may have at least one dimension that is even longer than 30 cm. In these cases, the test article may be first formed as an extended length or roll to which test pathogen is applied in a continuous process. Subsequently, a later process may singulate (e.g., cut, pinch, tear) or otherwise adapt the first formed test article into a plurality of final test articles.

In some cases, a vaginal endocavitary probe is on the order of two to four centimeters (2-4 cm) across a given diameter, along the length of the probe. In at least some cases, these probes do not have a sufficiently large "flat" spot on which to deposit the test-pathogen mixture. Nevertheless, the probe may still be suitably inoculated using the automated test-pathogen deposition system 100 via the test-pathogen dispenser 106 that is controllably moved in three dimensions.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An apparatus, comprising:
 a pathogen distribution mechanism, and a holding mechanism configured to removably secure a test article to said apparatus, said test article having at least one reference surface exposed to said pathogen distribution mechanism;
 whereon said pathogen distribution mechanism is configured to obtain a uniform distribution of a test-pathogen mixture across said at least one exposed reference surface of the test article;
 wherein said uniform distribution of the test-pathogen mixture comprises a deposition of a plurality of individual droplets,
 wherein said pathogen distribution mechanism comprises an automated positioning system configured to repeatably move a dispensing mechanism to a plurality of determined locations in proximity to the at least one exposed reference surface; and
 the automated dispensing system configured to direct the dispensing mechanism to repeatably introduce one or more portions of the test-pathogen mixture about a surface of said at least one exposed reference surface;
 wherein the automated positioning system is configured to repeatably position at least one orifice of the dispensing mechanism at a distance from said at least one exposed reference surface;
 wherein the automated positioning system comprises a control system programmed to generate at least one data structure representing a plurality of contours of said at least one exposed reference surface; and
 wherein the apparatus further comprises at least one distance sensor configured to determine the distance between the automated dispensing mechanism and the surface of said at least one exposed reference surface wherein the distance is utilized to determine a size, a shape, contours, or a three-dimensional (3-D) model of said at least one exposed the reference surface of the test article.

2. An apparatus according to claim 1 wherein the at least one exposed reference surface is treated with a chemical or non-chemical wetting agent, and wherein the at least one exposed reference surface has wetting properties.

3. An apparatus according to claim 1 wherein the at least one exposed reference surface is treated with a chemical agent modifying adhesion properties of said at least one exposed reference surface, and wherein the at least one exposed reference surface has adhesion properties.

4. The apparatus according to claim 1 wherein the test-pathogen mixture includes at least one type of virus, bacteria, fungus, yeast-mold, spore, or chemotherapeutic agent.

5. The apparatus according to claim 1 wherein at least a portion of said uniform distribution of the test-pathogen mixture includes a substantially homogeneous distribution of the test-pathogen mixture across the at least one exposed reference.

6. The apparatus according to claim 1 wherein said uniform distribution of the test-pathogen mixture includes a deposition of one or more continuous lines, each of the one or more continuous lines having a determined length and a determined width.

7. The apparatus according to claim 1 wherein said uniform distribution of the test-pathogen mixture includes a determined time-to-dry between applications of the one or more portions of the test-pathogen mixture.

8. The apparatus according to claim 1 wherein said uniform distribution of the test-pathogen mixture includes distribution of the test-pathogen mixture in a determined pattern.

9. The apparatus according to claim 1 wherein the automated positioning system controls movement of the dispensing mechanism in at least two dimensions.

10. The apparatus according to claim 1 wherein the automated positioning system comprises at least one distance sensor to determine a distance between the dispensing mechanism and the at least one exposed reference surface.

11. The apparatus according to claim 10 wherein the automated position system comprises at least one range sensor is for confirming a distribution of at least a portion of the test pathogen.

12. The apparatus according to claim 1 wherein the dispensing mechanism is arranged to form a defined volume of the test-pathogen mixture comprising a droplet at the at least one orifice and wherein the automated positioning system is arranged to permit the droplet to contact the at least one exposed reference surface.

13. The apparatus according to claim 12 wherein the dispensing mechanism comprises a dispenser tip, the dispenser tip having a substantially cylindrical shape or a substantially cannular shape.

14. The apparatus according to claim 13 wherein the dispenser tip is one of a plurality of dispenser tips.

15. The apparatus according to claim 12 wherein the dispensing mechanism comprises a device selected from the group consisting of a vibration device, an electrostatic charge generation device, a pump, a heater, and an aerator.

16. The apparatus according to claim 1 wherein the dispensing mechanism comprises a micro-droplet dispenser configured to introduce a substantially accurate volume of the test-pathogen mixture about the at least one exposed reference surface.

17. The apparatus according to claim 16 wherein the dispensing mechanism comprises a pressure control device, the pressure control device arranged to supply a positive pressure and a negative pressure, the positive pressure and the negative pressure arranged to form and hold the substantially accurate volume of the test pathogen at the at least one orifice of the dispensing mechanism.

18. The apparatus according to claim 12 wherein the droplet has a volume of between about between 0.001 μl and about 0.1 ml.

19. A method of manufacturing a test article for disinfection device testing, said method comprising:
preparing a test article, said test article being configured by a holding mechanism to be removably securable, wherein at least one reference surface of the test article is exposed; and
uniformly distributing a test-pathogen mixture across the at least one exposed reference surface of the test article with a pathogen distribution mechanism so that said test article is configured to be used for disinfection device testing wherein said pathogen distribution mechanism comprises an automated positioning system configured to repeatably move a dispensing mechanism to a plurality of determined locations in proximity to the at least one exposed reference surface; and
the automated dispensing system further configured to direct the dispensing mechanism to repeatably introduce one or more portions of the test-pathogen mixture about a surface of said at least one exposed reference surface;
wherein the automated positioning system is configured to repeatably position at least one orifice of the dispensing mechanism at a distance from said at least one exposed reference surface;
wherein the automated positioning system comprises a control system programmed to generate at least one data structure representing a plurality of contours of said at least one exposed reference surface; and
wherein the apparatus further comprises at least one distance sensor configured to determine the distance between the automated dispensing mechanism and the surface of said at least one exposed reference surface, the distance utilized to determine a size, a shape, contours, or a three-dimensional (3-D) model of said at least one exposed the reference surface of the test article.

20. A test article production device, comprising:
a base;
a holding mechanism coupled to the base, the holding mechanism configured to support a test article;
a gantry structure fixed relative to the base;
a test-pathogen dispenser movably secured relative to the gantry structure; and
at least one dispenser tip in fluid communication with the test-pathogen dispenser, the at least one dispenser tip arranged to deliver one or more portions of a uniform distribution of a test-pathogen mixture from the test-pathogen dispenser to the test article via the at least one dispenser tip, wherein the one or more portions of test pathogen have a determined volume;
wherein the uniform distribution of the test-pathogen mixture includes a deposition of a plurality of individual droplets;
wherein said pathogen distribution mechanism comprises an automated positioning system configured to repeatably move a dispensing mechanism to a plurality of determined locations in proximity to the at least one exposed reference surface; and
the automated dispensing system configured to direct the dispensing mechanism to repeatably introduce the one or more portions of the test-pathogen mixture about a surface of said at least one exposed reference surface;
wherein the automated positioning system is configured to repeatably position at least one orifice of the dispensing mechanism at a distance from said at least one exposed reference surface;
wherein the automated positioning system comprises a control system programmed to generate at least one data structure representing a plurality of contours of said at least one exposed reference surface; and
wherein the test article production device further comprises at least one distance sensor configured to determine the distance between the automated dispensing mechanism and the surface of said at least one exposed reference surface, the distance utilized to determine a size, a shape, contours, or a three-dimensional (3-D) model of said at least one exposed the reference surface of the test article.

21. The test article production device according to claim 20, further comprising a controller arranged to direct movement of either the test article or the at least one dispenser tip relative to each other, the controller further configured to direct formation of the one or more portions of said test-pathogen mixture.

22. The test article production device according to claim 21 wherein the controller is arranged to deliver the one or more portions of test-pathogen mixture to the test article in a determined pattern.

* * * * *